(12) United States Patent
Koglin et al.

(10) Patent No.: US 9,382,294 B2
(45) Date of Patent: Jul. 5, 2016

(54) BROAD SPECTRUM ANTIBIOTIC COMPOUNDS AND USE THEREOF

(71) Applicant: Los Alamos National Security, LLC, Los Alamos, NM (US)

(72) Inventors: Alexander Koglin, Los Alamos, NM (US); Matthias Strieker, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 14/771,710

(22) PCT Filed: Feb. 28, 2014

(86) PCT No.: PCT/US2014/019526
§ 371 (c)(1),
(2) Date: Aug. 31, 2015

(87) PCT Pub. No.: WO2014/134493
PCT Pub. Date: Sep. 4, 2014

(65) Prior Publication Data
US 2016/0009765 A1    Jan. 14, 2016

Related U.S. Application Data

(60) Provisional application No. 61/771,322, filed on Mar. 1, 2013.

(51) Int. Cl.
| | | |
|---|---|---|
| *C07H 19/02* | (2006.01) | |
| *C07H 17/00* | (2006.01) | |
| *A61K 38/00* | (2006.01) | |
| *C07K 9/00* | (2006.01) | |

(52) U.S. Cl.
CPC ............... *C07K 9/006* (2013.01); *C07H 17/00* (2013.01); *C07H 19/02* (2013.01); *A61K 38/00* (2013.01)

(58) Field of Classification Search
None
See application file for complete search history.

(56) References Cited

U.S. PATENT DOCUMENTS

| | | |
|---|---|---|
| 5,668,272 A | 9/1997 | Prasad et al. |
| 6,455,507 B1 | 9/2002 | Drach et al. |
| 2010/0222546 A1* | 9/2010 | Crich .................. C07K 1/02 530/322 |
| 2012/0108530 A1 | 5/2012 | Goff et al. |

OTHER PUBLICATIONS

Strieker et al., "Nonribosomal Peptide Synthetases: Structures and Dynamics," *Curr. Opin. Struct. Biol.*, vol. 20:234-240, 2010.

* cited by examiner

*Primary Examiner* — Traviss C McIntosh, III
(74) *Attorney, Agent, or Firm* — Klarquist Sparkman, LLP

(57) ABSTRACT

The discovery of a non-ribosomal peptide synthetase (NRPS) gene cluster in the genome of *Clostridium thermocellum* that produces a secondary metabolite that is assembled outside of the host membrane is described. Also described is the identification of homologous NRPS gene clusters from several additional microorganisms. The secondary metabolites produced by the NRPS gene clusters exhibit broad spectrum antibiotic activity. Thus, antibiotic compounds produced by the NRPS gene clusters, and analogs thereof, their use for inhibiting bacterial growth, and methods of making the antibiotic compounds are described.

25 Claims, 6 Drawing Sheets

BROAD SPECTRUM ANTIBIOTIC COMPOUNDS AND USE THEREOF

CROSS REFERENCE TO RELATED APPLICATIONS

This is the U.S. National Stage of International Application No. PCT/US2014/019526, filed Feb. 28, 2014, published in English under PCT Article 21(2), which claims the benefit of U.S. Provisional Application No. 61/771,322, filed Mar. 1, 2013, which is herein incorporated by reference in its entirety.

ACKNOWLEDGMENT OF GOVERNMENT SUPPORT

This invention was made with government support under Contract No. DE-AC52-06NA25396 awarded by the U.S. Department of Energy. The government has certain rights in the invention.

FIELD

This disclosure concerns antibiotic compounds produced by non-ribosomal peptide synthetase gene clusters found in microbial organisms, the use of such compounds for inhibiting microbial growth and treating microbial infections, and methods of making the antibiotic compounds.

BACKGROUND

Antibiotics transformed medicine dramatically by providing efficient treatments against bacterial infections causing severe illnesses and death. However, the emergence of antibiotic resistance is significantly reducing the efficacy of antibiotic treatments and bacterial infections have become a major public health threat again. Gram-negative bacteria like *Acinetobacter baumannii* and *Pseudomonas aeruginosa*, and gram-positive bacteria such as *Staphylococcus aureus* or *Clostridium difficile*, are rapidly evolving resistance against multiple antibiotics. The endemic appearance of bacterial pathogens in hospitals, health care facilities and water treatment plants is causing an additional threat.

Until 15-20 years ago, new antibiotics were developed in time to counter emerging resistant bacteria. However, this pipeline of new antibiotics has dried up as the development of new antibodies is no longer a focus for pharmaceutical companies. For example, *A. baumannii*, *S. aureus* and *M. tuberculosis* are causing untreatable infections due to the emergence of resistance even against antibiotics of last resort. While the emergence of drug resistance among natural bacteria is of immense concern, man-made pathogens pose an additional threat. New antibiotics, particularly those that can treat infections with multidrug resistant bacteria, are therefore in dire need.

SUMMARY

According to one embodiment disclosed herein, there is provided an antibiotic compound, or a pharmaceutically acceptable salt, ester, hydrate or solvate thereof, comprising Formula I:

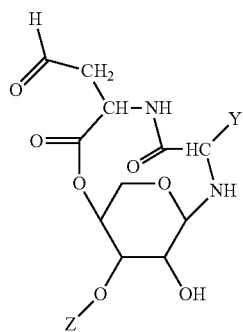

where Y is $C_1$-$C_{10}$ alkyl, and Z is hydrogen, —OH, or a monosaccharide.

In some embodiments, the antibiotic compound has the stereochemistry of Formula II:

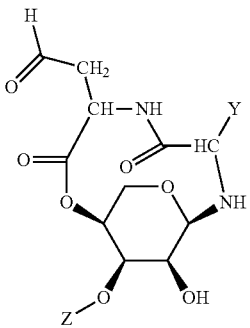

In one non-limiting example, the antibiotic compound (referred to herein as Compound #1) comprises the structure:

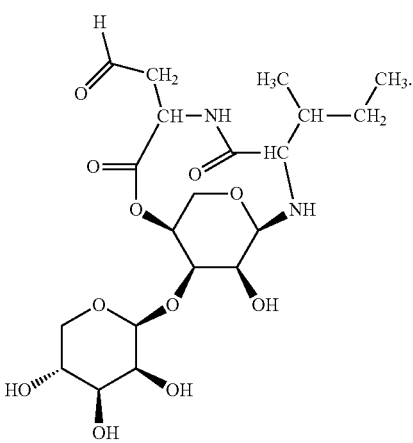 [SMILES: CCC(C)C1N[C@@H]2OC[C@H](OC(=O)C(CC=O)NC1=O)[C@H](O[C@@H]1OC[C@@H](O)[C@H](O)[C@@H]1O)[C@@H]2O]

Further provided is a method of inhibiting microbial growth, such as bacterial growth, by contacting the microorganisms with an antibiotic compound disclosed herein. In some embodiments, the method of inhibiting microbial growth is an in vitro method. In other embodiments, the method is an in vivo method that includes administering the antibiotic compound to a subject with a microbial, such as a bacterial, infection.

Also provided herein is a method of treating a microbial infection (such as a bacterial infection) in a subject by selecting a subject in need of treatment and administering to the subject a therapeutically effective amount of an antibiotic compound disclosed herein.

Methods of making the disclosed antibiotic compounds are also provided by the present disclosure.

The foregoing and other objects, features, and advantages of the invention will become more apparent from the following detailed description, which proceeds with reference to the accompanying figures.

SEQUENCE LISTING

Figure 1:
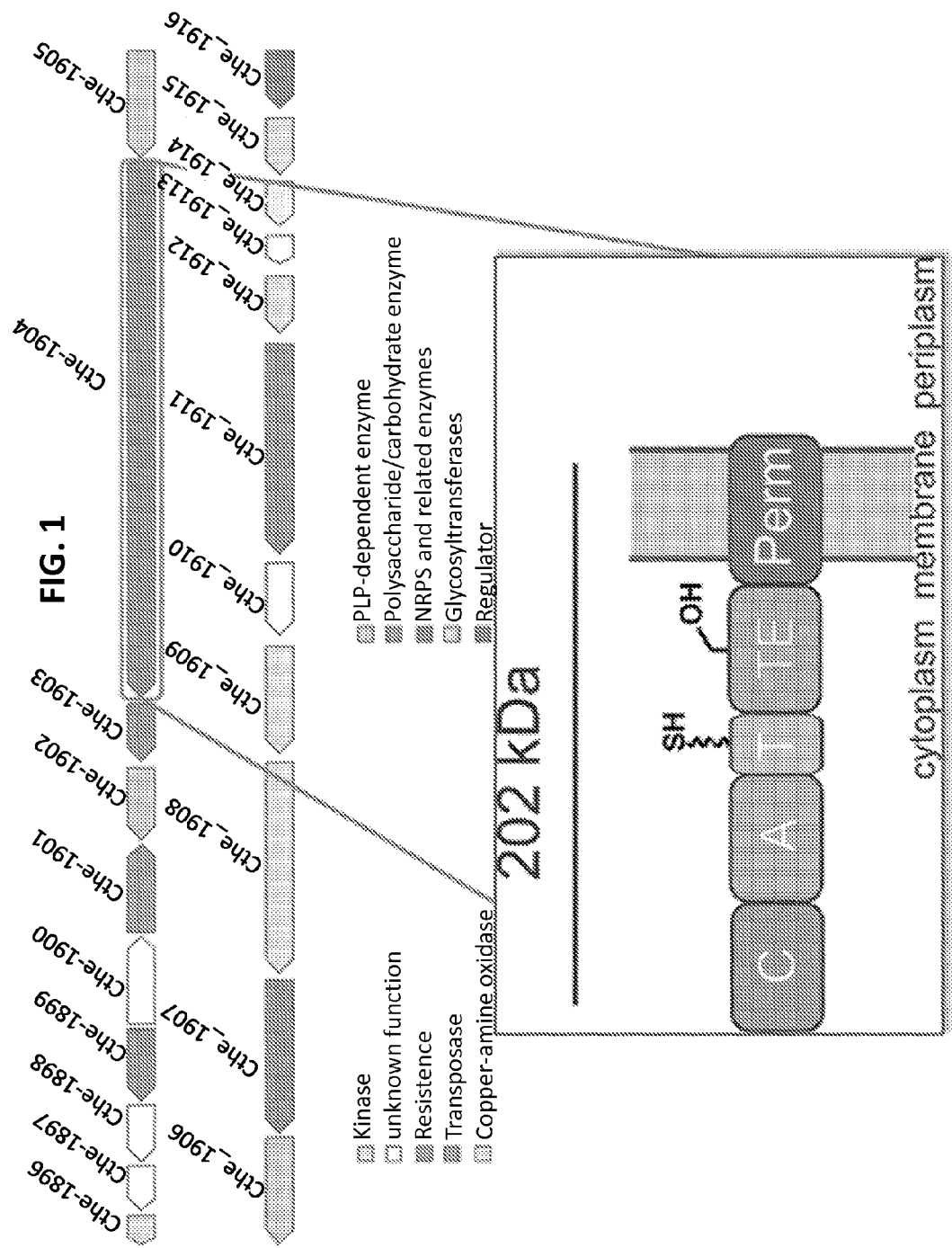
FIG. 1 is a schematic of the non-ribosomal peptide synthetase (NRPS) gene cluster identified in *Clostridium thermocellum*. The genes identified, and the functions of the encoded proteins, are shown. C=condensation domain; A=adenylation domain; T=thiolation domain; TE=termination domain; Perm=maltose-permease homologue transporter.

The amino acid sequences listed in the accompanying Sequence Listing are shown using standard three letter code for amino acids, as defined in 37 C.F.R. 1.822. The Sequence Listing is submitted as an ASCII text file, created on Aug. 23, 2015, 70 KB, which is incorporated by reference herein. In the accompanying Sequence Listing:

SEQ ID NO: 1 is the amino acid sequence of the amino acid adenylation domain from *Clostridium thermocellum* strain DSM4150.

SEQ ID NO: 2 is the amino acid sequence of the amino acid adenylation domain from *Herpetosiphon aurantiacus* strain DSM 785.

SEQ ID NO: 3 is the amino acid sequence of the amino acid adenylation enzyme/thioester reductase family protein from *Streptosporangium roseum* strain DSM 43021.

SEQ ID NO: 4 is the amino acid sequence of the amino acid adenylation enzyme/thioester reductase family protein from *Catenulispora acidiphila* strain DSM 44928.

SEQ ID NO: 5 is the amino acid sequence of the sugar transporter protein from *Pyrobaculum aerophilum*.

SEQ ID NO: 6 is the amino acid sequence of a putative NRPS related protein from *Emericella nidulans*.

DETAILED DESCRIPTION

I. Abbreviations
   CIP ciprofloxacin
   DMSO dimethylsulfoxide
   HPLC high pressure liquid chromatography
   MIC minimum inhibitory concentration
   MTD maximum tolerated dose
   NMR nuclear magnetic resonance
   NRPS non-ribosomal peptide synthetase
   TLC thin layer chromatography
   VAN vancomycin II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administer: As used herein, administering a composition (e.g. an antibiotic compound) to a subject means to give, apply or bring the composition into contact with the subject. Administration can be accomplished by any of a number of routes, such as, for example, topical, oral, subcutaneous, intramuscular, intraperitoneal, intravenous, intrathecal and intramuscular.

Alkyl: A hydrocarbon group having a saturated carbon chain. The chain may be cyclic, branched or unbranched. The chain may unsubstituted, or substituted with one or more substituents. Exemplary substituents include, for example and without limitation, hydroxyl, amine, amide, sulfonamide, halo, cyano, carboxy, mercapto, alkyl, alkoxy, alkylthio, thioalkoxy, arylalkyl, heteroaryl, alkylamino, oxy, and dialkylamino.

Amino acid: Amino acid refers to both natural and unnatural amino acids, including their D and L stereoisomers for chiral amino acids. Natural and unnatural amino acids are well known to those of ordinary skill in the art. Common natural amino acids include, without limitation, alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val). Uncommon and unnatural amino acids include, without limitation, allyl glycine (AllylGly), biphenylalanine (Bip), citrulline (Cit), 4-guanidinophenylalanine (Phe(Gu)), homoarginine (hArg), homolysine (hLys), 2-napthylalanine (2-Nal), ornithine (Orn) and pentafluorophenylalanine (F5Phe).

Amino acids are typically classified in one or more categories, including polar, hydrophobic, acidic, basic and aromatic, according to their side chains. Examples of polar amino acids include those having side chain functional groups such as hydroxyl, sulfhydryl, and amide, as well as the acidic and basic amino acids. Polar amino acids include, without limitation, asparagine, cysteine, glutamine, histidine, selenocysteine, serine, threonine, tryptophan and tyrosine. Examples of hydrophobic or non-polar amino acids include those residues having nonpolar aliphatic side chains, such as, without limitation, leucine, isoleucine, valine, glycine, alanine, proline, methionine and phenylalanine. Examples of basic amino acid residues include those having a basic side chain, such as an amino or guanidino group. Basic amino acid residues include, without limitation, arginine, homolysine and lysine. Examples of acidic amino acid residues include those having an acidic side chain functional group, such as a carboxy group. Acidic amino acid residues include, without limitation aspartic acid and glutamic acid. Aromatic amino acids include those having an aromatic side chain group. Examples of aromatic amino acids include, without limitation, biphenylalanine, histidine, 2-napthylalananine, pentafluorophenylalanine, phenylalanine, tryptophan and tyrosine. It is noted that some amino acids are classified in more than one group, for example, histidine, tryptophan and tyrosine are classified as both polar and aromatic amino acids. Additional amino acids that are classified in each of the above groups are known to those of ordinary skill in the art.

Analog, derivative or mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, and/or a change in ionization. Structural analogs are often found using quantitative structure activity relationships (QSAR), with techniques such as those disclosed in Remington (*The Science and Practice of Pharmacology,* 19th Edition (1995), chapter 28). When the changes to the original compound are substantial, or many incremental changes are combined, the compound is no longer an analog. A derivative is a biologically active molecule derived from the base structure. A mimetic is a molecule that mimics the activity of another molecule by mimicking the structure of such a molecule, such as a biologically active molecule. Thus, the term "mimetic" indicates a definite structure related to activity.

Antibiotic: A substance often produced by or derived from certain fungi, bacteria, and other organisms, that can destroy or inhibit the growth of other microorganisms. Antibiotics can also be synthetically produced.

*Aspergillus nidulans*: A type of filamentous fungi in the phylum Ascomycota. It is one of the few species in its genus capable of forming sexual spores through meiosis. *A. nidulans* is also called *Emericella nidulans* when referring to its sexual form.

*Catenulispora acidiphila*: A Gram-positive, filamentous, acidophilic bacterium first isolated from forest soil.

*Clostridium thermocellum*: An anaerobic, thermophilic bacterium capable of converting cellulosic substrates into ethanol. The complete genome sequence of *C. thermocellum* (ATCC 27405) is available in GENBANK™ under NCBI reference number NC_009012, which is herein incorporated by reference as it appears in the database on Dec. 8, 2011.

Condensation: A reaction in which two molecules combine to form a single molecule, accompanied by the loss of a small molecule, e.g., water, methanol, acetic acid, or a hydrogen halide.

Contacting: Placement in direct physical association; includes both in solid and liquid form.

Coupling: Joining a first unit to a second unit. This includes, but is not limited to, covalently bonding one molecule to another molecule, noncovalently bonding one molecule to another (e.g., electrostatically bonding), non-covalently bonding one molecule to another molecule by hydrogen bonding, non-covalently bonding one molecule to another molecule by van der Waals forces, and any and all combinations of such couplings.

Gene cluster: A set of genetic elements grouped together on the chromosome, the protein products of which have a related function, such as forming a natural product biosynthetic pathway.

Gram-positive bacteria: Bacteria having a cell wall composed of a thick layer of peptidoglycan. Gram-positive bacteria retain the color of the crystal violet stain in the Gram method of staining Exemplary Gram-positive bacteria include *Staphylococcus aureus, Streptococcus pneumoniae, Bacillus subtilis,* and *Clostridium difficile.*

Gram-negative bacteria: Bacteria having a cell wall composed of a thin layer of peptidoglycan. Gram-negative bacteria lose the crystal violet stain and take the color of the red counterstain in Gram's Method of staining. Gram-negative bacteria include most of the bacteria normally found in the gastrointestinal tract. Exemplary Gram-negative bacteria include *Pseudomonas aeruginosa, Salmonella enterica, Pseudomonas putida, Escherichia coli, Acinetobacter baumannii* and *Haemophilus influenzae.*

*Herpetosiphon aurantiacus*: A filamentous, Gram-negative bacterium that grows in long, flexible filaments. This bacterium was first isolated from Lake Birch in Minnesota in 1968.

Homologous amino acid sequence: An amino acid sequence that differs from an amino acid sequence by one or more conservative amino acid substitutions. Homologous sequences also encompass allelic variants as well as sequences containing deletions or insertions which retain the functional characteristics of the polypeptide. In some instances, such a sequence is at least 75%, at least 80%, at least 85%, at least 90%, at least 95%, or at least 98% identical to any one of the amino acid sequences disclosed herein.

Homologous amino acid sequences include sequences that are identical or substantially identical to the amino acid sequences set forth in the sequence listing. By "substantially identical to the amino acid sequence" it is meant a sequence that is at least 90%, at least 95%, at least 97%, or at least 99% identical to an amino acid sequence of reference. In an example, the sequence is at least 90% identical and differs from the sequence of reference by conservative amino acid substitutions. Polypeptides having a sequence homologous to any one of the amino acid sequences disclosed herein include naturally-occurring allelic variants, as well as mutants or any other non-naturally occurring variants that retain the inherent characteristics (e.g., biosynthetic activity) of any polypeptide providing herein. Homology can be measured using sequence analysis software such as Sequence Analysis Software Package of the Genetics Computer Group, University of Wisconsin Biotechnology Center, 1710 University Avenue, Madison, Wis. 53705 Amino acid sequences can be aligned to maximize identity. Gaps can also be artificially introduced into the sequence to attain optimal alignment. Once the optimal alignment has been set up, the degree of homology is established by recording all of the positions in which the amino acids of both sequences are identical, relative to the total number of positions. Homologous polynucleotide sequences are defined in a similar way. In some embodiments, a homologous sequence is one that is at least 45%, 50%, 60%, 70%, 75%, 80%, 85%, 86%, 87%, 88%, 89%, 90%, 91%, 92%, 93%, 94%, 95%, 96%, 97%, 98%, 99% or identical to any one of the sequences disclosed herein.

Inhibiting bacterial growth: Reducing or eliminating bacterial replication and/or spread, in vitro or in vivo. Inhibition need not be complete inhibition. In some embodiments, inhibition of bacterial growth is inhibition of at least 10%, at least 20%, at least 30%, at least 40%, at least 50%, at least 60%, at least 70% or at least 80%. Similarly, inhibiting microbial growth refers to reducing or eliminating microbial (such as bacterial or fungal) replication and/or spread in vitro or in vivo.

Isolated: An isolated biological component (such as a nucleic acid molecule, organic compound or protein) is one that has been substantially separated or purified away from other biological components in the cell of the organism in which the component naturally occurs, such as other chromosomal and extra-chromosomal DNA and RNA, proteins and organelles. With respect to nucleic acids and/or polypeptides, the term can refer to nucleic acids or polypeptides that are no longer flanked by the sequences typically flanking them in nature. Nucleic acids and proteins that have been isolated include nucleic acids and proteins purified by standard purification methods. The term also embraces nucleic acids and proteins prepared by recombinant expression in a host cell as well as chemically synthesized nucleic acids and proteins.

Mitsunobu reaction: An organic reaction that allows the conversion of primary and secondary alcohols to amines, esters, phenyl ethers, thioethers, and various other compounds. Conversion of an alcohol to an amine typically includes reaction of the alcohol with triphenylphosphine, diethyl azodicarboxylate (DEAD), and a nitrogen nucleophile (e.g., phthalimide), followed by subsequent hydrolysis or selective reduction.

Monosaccharide: A simple, monomeric sugar. With few exceptions, a monosaccharide has the basic chemical formula $C_x(H_2O)_y$, where x and y are integers, and x is at least 3. Typically, y=x or y=x−1. Many monosaccharides are pentoses (x=5) or hexoses (x=6). Examples of monosaccharides include arabinose, fructose, galactose, glucose, ribose, and xylose, among others. A disaccharide is a dimer formed by two monosaccharides linked together by a glycosidic bond. Disaccharides include both hetero-dimers and homo-dimers.

*Myxococcus xanthus*: A rod-shaped, Gram-negative bacterium that grows in colonies that exhibit self-organizing behavior.

Nonribosomal peptide synthetase (NRPS): A large multifunctional protein that synthesizes polypeptides by a nonribosomal mechanism, often known as thiotemplate synthesis (Kleinkauf and von Doehren *Ann. Rev. Microbiol.* 41: 259-289, 1987). Such nonribosomal polypeptides can have a linear, cyclic, or branched cyclic structure and often contain amino acids not present in proteins or amino acids modified through methylation or epimerization. NRPSs are typically organized into modules. A "module" is a set of distinctive domains that encode all the enzyme activities necessary for one cycle of peptide chain elongation and associated modifications. The number and order of modules and the type of domains within a module on each NRPS protein determine the structural variations of the resulting peptide products by dictating the number, order, choice of the amino acid to be incorporated, and the modifications associated with a particular cycle of elongation. The modular architecture of NRPS (Cane et al. *Science* 282: 63-68, 1998, Stachelhaus et al. *Science* 269: 69-72, 1995; Stachelhaus et al. *Mol. Gen. Genet.* 257: 308-318, 1998; and Belshaw et al. *Science* 284:486-489, 1999) has been successfully used in combinatorial biosynthesis of diverse natural product analogs.

Typically, the enzyme organization of an NRPS gene cluster is such that the modules occur in the primary sequence in the same order that the amino acids are assembled into the peptide product (colinearity principle). There are three components to the minimum extending module. The adenylation (A) domain recognizes a specific amino acid and uses ATP to activate the carboxyl as the adenylate. This facilitates attachment of the carboxyl to the thiol of a 4'-phosphopanteteheine (p-pant) cofactor attached to the peptidyl carrier (PCP, or thiolation (T)) domain. The third domain is the condensation (C) domain that catalyzes formation of peptide bonds between amino acids or peptides attached to PCP domains or adjacent modules, thereby promoting directional peptide chain elongation. The order of these domains in a typical module is C-A-T.

Oligomer: A general term for a polymeric molecule consisting of relatively few monomers, e.g., ≤10 monomers.

Oligopeptide: An oligomer in which the monomers are amino acid residues that are joined together through amide bonds.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compositions, such as one or more antibiotic compounds.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease (such as an infection) refers to inhibiting the full development of a disease. "Treating" refers to a therapeutic intervention that ameliorates a sign or symptom of a disease or pathological condition after it has begun to develop. "Ameliorating" refers to the reduction in the number or severity of one or more signs or symptoms of a disease.

Protecting or protective group: When synthesizing organic compounds, often some specific functional groups cannot survive the required reagents or chemical environments. These groups must be protected. A protecting group, or protective group, is introduced into a molecule by chemical modification of a functional group in order to obtain chemoselectivity in a subsequent chemical reaction. Various exemplary protecting or protective groups are disclosed in Greene's Protective Groups in Organic Synthesis, by Peter G. M. Wuts and Theodora W. Greene (Oct. 30, 2006), which is incorporated herein by reference.

Purified: The term purified does not require absolute purity; rather, it is intended as a relative term. Thus, for example, a purified protein preparation is one in which the protein referred to is more pure than the protein in its natural environment within a cell.

*Pyrobaculum aerophilum*: A rod-shaped hyperthermophilic archaebacterium with an optimal growth temperature of 100° C. and pH of 7.0.

*Rickettsia conorii*: A unicellular, gram-negative, obligate intracellular bacterium of the genus *Rickettsia*.

Secondary metabolite: An organic compound that is not directly involved in the normal growth, development or reproduction of an organism. Secondary metabolites often play a role in host defense (e.g., antibiotics).

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences.

Methods for aligning sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; Huang, et al., *Computer Applications in the Biosciences* 8:155-165, 1992; Pearson et al., *Methods in Molecular Biology* 24:307-331, 1994; Tatiana et al., (1999), *FEMS Microbiol. Lett.*, 174:247-250, 1999. Altschul et al. present a detailed consideration of sequence-alignment methods and homology calculations (*J. Mol. Biol.* 215:403-410, 1990).

The National Center for Biotechnology Information (NCBI) Basic Local Alignment Search Tool (BLAST™, Altschul et al., *J. Mol. Biol.* 215:403-410, 1990) is available from several sources, including the National Center for Biotechnology Information (NCBI, Bethesda, Md.) and on the Internet, for use in connection with the sequence-analysis programs blastp, blastn, blastx, tblastn and tblastx. A description of how to determine sequence identity using this program is available on the internet under the help section for BLAST™.

For comparisons of amino acid sequences of greater than about 30 amino acids, the "Blast 2 sequences" function of the BLAST™ (Blastp) program is employed using the default BLOSUM62 matrix set to default parameters (cost to open a gap [default=5]; cost to extend a gap [default=2]; penalty for a mismatch [default=−3]; reward for a match [default=1]; expectation value (E) [default=10.0]; word size [default=3]; number of one-line descriptions (V) [default=100]; number of alignments to show (B) [default=100]). When aligning short peptides (fewer than around 30 amino acids), the alignment should be performed using the Blast 2 sequences function, employing the PAM30 matrix set to default parameters (open gap 9, extension gap 1 penalties). Proteins (or nucleic acids) with even greater similarity to the reference sequences will show increasing percentage identities when assessed by this method, such as at least 50%, at least 60%, at least 70%, at least 80%, at least 85%, at least 90%, or at least 95% sequence identity.

For comparisons of nucleic acid sequences, the "Blast 2 sequences" function of the BLAST™ (Blastn) program is employed using the default BLOSUM62 matrix set to default parameters (cost to open a gap [default=11]; cost to extend a gap [default=1]; expectation value (E) [default=10.0]; word size [default=11]; number of one-line descriptions (V) [default=100]; number of alignments to show (B) [default=100]). Nucleic acid sequences with even greater similarity to the reference sequences will show increasing percentage identities when assessed by this method, such as at least 60%, at least 70%, at least 75%, at least 80%, at least 85%, at least 90%, at least 95%, or at least 98% sequence identity.

Nucleic acid sequences that do not show a high degree of identity can nevertheless encode similar amino acid sequences, due to the degeneracy of the genetic code. It is understood that changes in nucleic acid sequence can be made using this degeneracy to produce multiple nucleic acid molecules that all encode substantially the same protein.

*Streptosporangium roseum*: An aerobic, Gram-positive bacterium first isolated from vegetable garden soil in 1955.

Subject: Living multi-cellular vertebrate organisms, a category that includes both human and non-human mammals.

Therapeutically effective amount: A quantity of a specified agent (such as an antibiotic compound) sufficient to achieve a desired effect in a subject being treated with that agent. For example, this may be the amount of an antibiotic compound useful for treating a bacterial infection in a subject. In the context of the present disclosure, a therapeutically effective amount of an antibiotic compound, for example, is an amount sufficient to treat a microbial infection in a subject (e.g., reduce or eliminate infectious organisms from the subject) without causing a substantial cytotoxic effect in the subject. The effective amount of an antibiotic compound useful for treating a microbial infection in a subject will be dependent on, for example, the subject being treated, the type of infection being treated, the manner of administration of the therapeutic composition and other factors.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

Disclosed herein is the discovery of a non-ribosomal peptide synthetase (NRPS) gene cluster that produces a bioactive compound that is assembled outside of its host membrane. The NRPS gene cluster was first identified in *Clostridium thermocellum*; however, several additional microorganisms were identified that encode an NRPS gene cluster. The metabolite was isolated from *Clostridium thermocellum*, and the structure was assigned by nuclear magnetic resonance spectroscopy and mass spectrometry. The compound (referred to herein as Compound #1) is a small, previously unknown glycopeptide that possesses broad-spectrum antibiotic activity against both Gram positive and Gram negative bacteria. Also described herein is the isolation of a second compound (Compound #2) produced by an NRPS gene cluster in *Herpetosiphon aurantiacus*. An antibiotic secondary metabolite has also been isolated from *Emericella nidulans* and is referred to herein as Compound #3.

IV. Overview of Several Embodiments

Disclosed herein is the identification of a NRPS gene cluster in *Clostridium thermocellum*, as well as homologous NRPS gene clusters in several additional microorganisms, including *Herpetosiphon aurantiacus, Myxococcus xanthus, Streptosporangium roseum, Catenulispora acidiphila, Pyrobaculum aerophilum, Rickettsia conorii* and *Emericella nidulans*. The NRPS gene clusters produce a secondary metabolite with broad spectrum antibiotic activity.

Thus, provided herein are broad spectrum antibiotic compounds synthesized by NRPS gene clusters of microorganisms. Also provided are methods of making such compounds, either by isolating the compounds from microbial cultures or by synthesizing the compounds. Methods of inhibiting bacterial growth in vitro and in vivo using the disclosed compounds are further provided by the present disclosure.

In some embodiments disclosed herein, provided is an antibiotic compound, or a pharmaceutically acceptable salt, ester, hydrate or solvate thereof, represented by the Formula I:

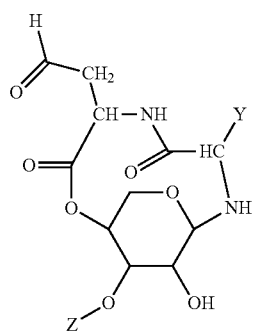

Formula I where Y is $C_1$-$C_{10}$ alkyl, and Z is hydrogen, —OH, or a monosaccharide.

In some examples, Y is a branched $C_4$ alkyl, such as, but not limited to, —CH(CH$_3$)CH$_2$CH$_3$. In some examples, Z is a hexose, such as, but not limited to, xylose.

In some embodiments, the antibiotic compounds comprise the stereochemistry of Formula II:

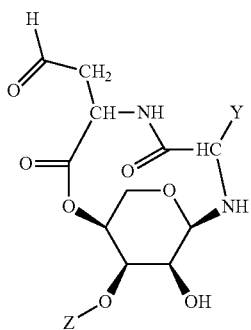

Formula II

In one non-limiting example, the antibiotic compound has the structure:

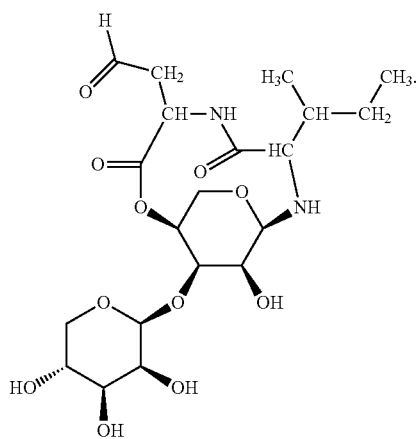 [SMILES: CCC(C)C1N[C@@H]2OC[C@H](OC(=O)C(CC=O)NC1=O)[C@H](O[C@@H]1OC[C@@H](O)[C@H](O)[C@@H]1O)[C@@H]2O]

Further provided is a method of inhibiting bacterial growth by contacting the bacteria with an antibiotic compound disclosed herein. In some embodiments, the bacteria are Gram-positive bacteria. For example, the Gram-positive bacteria may be selected from *Staphylococcus aureus, Streptococcus pneumoniae, Bacillus subtilis* and *Clostridium difficile*. In other embodiments, the bacteria are Gram-negative bacteria. In some examples, the Gram-negative bacteria are selected from *Pseudomonas aeruginosa, Salmonella enterica, Pseudomonas putida, Escherichia coli, Acinetobacter baumannii* and *Haemophilus influenzae*. In some embodiments, the bacteria is a species of *Mycobacterium*, such as, but not limited to, *Mycobacterium bovis* or *Mycobacterium tuberculosis*.

In some embodiments of the present disclosure, the method of inhibiting bacterial growth is an in vitro method. In other embodiments, the method of inhibiting bacterial growth is an in vivo method. In some examples of the in vivo method, contacting the bacteria with the compound comprises administering a therapeutically effective amount of the compound to a subject infected with the bacteria.

Also provided herein is a method of treating a bacterial infection in a subject by selecting a subject in need of treatment and administering to the subject a therapeutically effective amount of an antibiotic compound disclosed herein. In some embodiments, the subject in need of treatment is a subject with a bacterial infection, such as an infection with Gram-positive bacteria, Gram-negative bacteria or Mycobacteria.

In some examples of the disclosed methods, the subject is a non-human animal. In other examples, the subject is a human.

Also provided herein is a method of making a compound according to Formula I, where Y is $C_1$-$C_{10}$ alkyl, and Z is hydrogen, —OH, or a monosaccharide. In some embodiments, the method comprises:

providing a first amino acid according to the formula Y—CH(NHnOS)C(O)OH, where nOS is a protecting group;

providing a homoserine analog according to the formula R"OCH$_2$CH$_2$CH(NH$_2$)C(O)OH where R" is a protecting group;

coupling the first amino acid to the homoserine analog to form an amino acid dimer;

providing a carbohydrate precursor having the structure

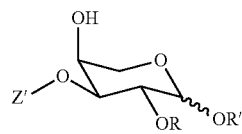

where R and R' are protecting groups, and Z' is hydrogen, R'" where R'" is a protecting group, or a monosaccharide precursor comprising one or more protecting groups in place of hydroxyl groups;

coupling the amino acid dimer to the carbohydrate precursor, thereby forming the structure

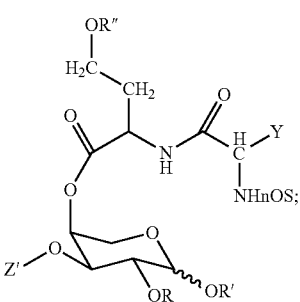

cyclizing the amino acid dimer and carbohydrate precursor, thereby forming the structure

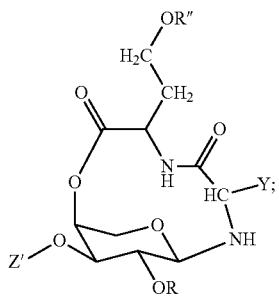

removing protecting groups to form hydroxyl groups, wherein the protecting groups comprise R, R''' and, when Z' is R''', R'''; and oxidizing the hydroxyl group formed by removal of R'', thereby forming the compound according to Formula I.

In some embodiments of the method for making the compound of Formula I, the first amino acid and the homoserine analog are coupled via an intermolecular condensation reaction using 1-mesitylene-2-fulsonyl-3-nitro-1,2,4-triazole.

In some embodiments, the amino acid dimer is coupled to the carbohydrate precursor via pentafluorophenyl ester coupling. In some examples, the amino acid dimer and carbohydrate precursor are cyclized via a Mitsunobu reaction.

In some embodiments of the method for making the compound of Formula I, R is p-methoxybenzyl ether, R' is n-pentenyl, and R'' is tert-butyldimethylsilyl ether.

In some embodiments, Z is xylose and providing the carbohydrate precursor further comprises:

providing first and second monosaccharide precursors having the structures

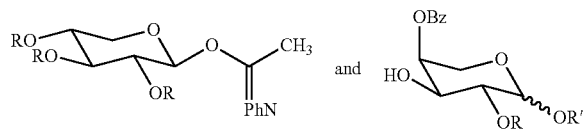

where R, R', and Bz are protecting groups p-methoxybenzyl ether, n-pentenyl, and benzoyl, respectively, and Ph is phenyl; and coupling the first and second monosaccharide precursors to form the carbohydrate precursor, wherein the carbohydrate precursor has the structure

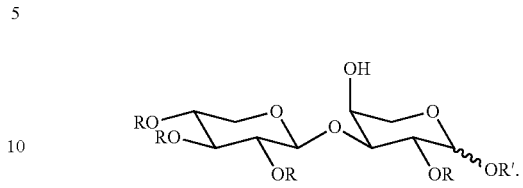

In some examples, the first and second monosaccharide precursors are coupled via an intermolecular condensation reaction using trimethylsilyl trifluoromethanesulfonate.

The present disclosure provides antibiotic compounds substantially as hereinbefore described, wherein the antibiotic compounds are isolated from a microorganism or synthesized as hereinbefore described.

Also provided is a method of isolating the disclosed antibiotic compounds as described in Example 2, 3 or 6.

V. Identification of Non-Ribosomal Peptide Synthetase (NRPS) Gene Clusters

Figure 2:
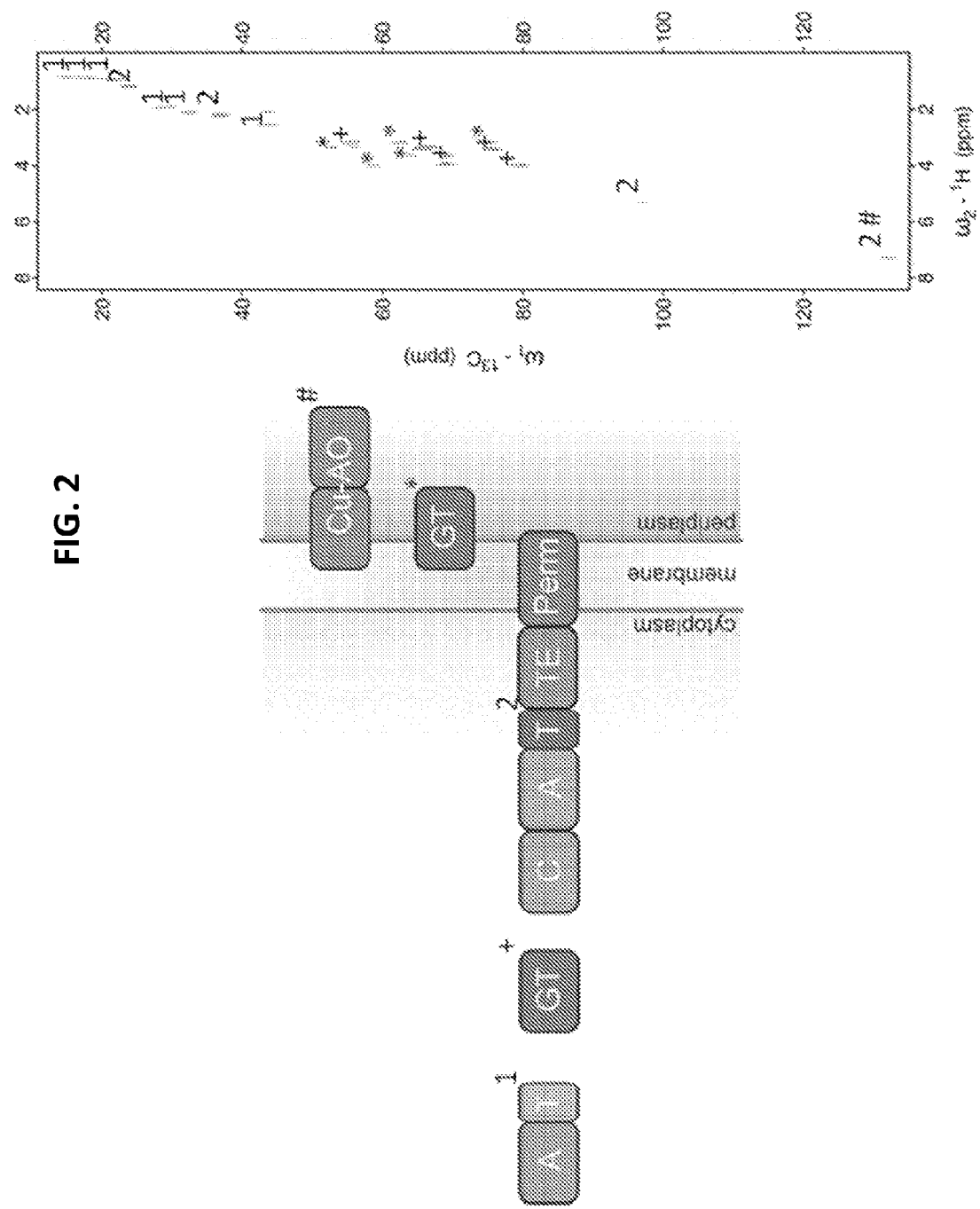
FIG. 2 shows a schematic of the proteins identified in the NRPS cluster and their assignments in a $^{13}$C-$^{1}$H HSQC NMR spectra recorded of the purified compound. C=condensation domain; A=adenylation domain; T=thiolation domain; TE=termination domain; Perm=maltose-permease homologue transporter; GT=glycosyltransferase; Cu-AO=copper-containing amine oxidase.

Described herein is the discovery of a new non-ribosomal peptide synthetase (NRPS) cluster for the biosynthesis of an unusual, novel secondary metabolite in the sequenced genome of the hyper-thermophilic anaerobic bacteria *Clostridium thermocellum* (FIG. 1). The enzymatic functions of the encoded proteins of this novel NRPS assembly line were identified (FIG. 2). The assumed secondary metabolite appeared unusual as additional unique enzymatic functions were associated with its biosynthesis, including glycosyltransferases and a copper coordinating amine-oxidase. The chemical structure of the new small glyco-peptide was proposed and its biosynthetic pathway was reconstructed in vitro by analyzing the order of the enzymatic functions associated with this NRPS cluster. The chemical structure of the isolated natural product (referred to herein as Compound #1) was analyzed by mass spectrometry and NMR spectroscopy.

Figure 6:
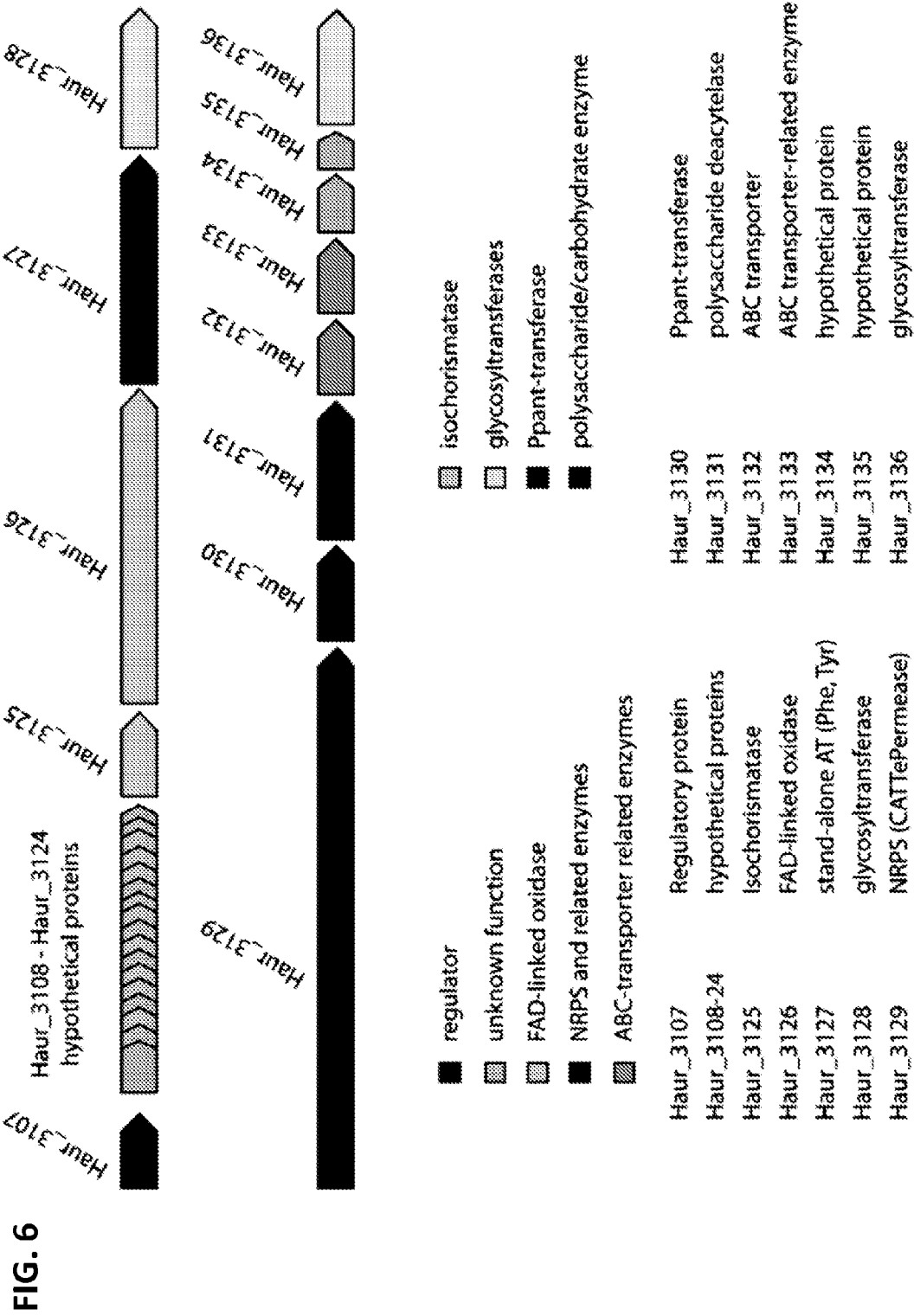
FIG. 6 is a schematic of a NRPS gene cluster identified in *Herpetosiphon aurantiacus*.

Also disclosed herein is the identification of homologous NRPS gene clusters in several additional microorganisms, including *Herpetosiphon aurantiacus, Myxococcus xanthus, Streptosporangium roseum, Catenulispora acidiphila, Pyrobaculum aerophilum, Rickettsia conorii* and *Emericella nidulans*. A schematic of the NRPS gene cluster identified in *Herpetosiphon aurantiacus* is shown in FIG. 6. In addition, the amino acid sequences of the adenylation domains (A domains) or homologous proteins from *Clostridium thermocellum, Herpetosiphon aurantiacus, Streptosporangium roseum, Catenulispora acidiphila, Pyrobaculum aerophilum* and *Emericella nidulans* are set forth herein as SEQ ID NOs: 1-6, respectively. The antibiotic secondary metabolites produced by the NRPS clusters of *Herpetosiphon aurantiacus* and *Emericella nidulans* have also been isolated and are referred to in the Examples as Compound #2 and Compound #3, respectively.

Further described herein are studies demonstrating the antibiotic activity of Compound #1, Compound #2 and Compound #3 against several Gram-positive and Gram-negative bacterial pathogens. As described in the Examples below, these antibiotic compounds are not toxic to mammalian cells and are well tolerated in vivo.

The antibiotic secondary metabolites produced by *C. thermocellum* and *H. aurantiacus* do not show any similarities to any currently known antibiotics. It is likely that the host organisms themselves are susceptible to their own metabolite based on the organization of the biosynthetic pathway that assembles cytosolic precursors in the periplasm. This suggests that evolution of antibiotic resistance against these compounds will not be easily accomplished.

VI. Antibiotic Compounds

A. Structure

Embodiments of the disclosed antibiotic compounds comprise at least one monosaccharide moiety and an oligopeptide moiety, which forms a cyclic structure with the monosaccharide. In some embodiments, the oligopeptide moiety is a dipeptide. In certain embodiments, the antibiotic compound comprises a disaccharide moiety and an oligopeptide moiety, which forms a cyclic structure with one of the monosaccharides. In some embodiments, an antibiotic compound has a structure according to Formula I:

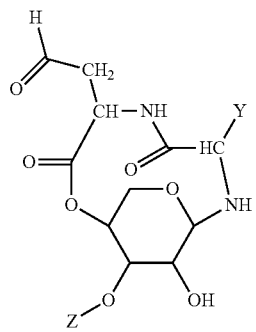

Formula I

With reference to Formula I, Y is $C_1$-$C_{10}$ alkyl, and Z is hydrogen, —OH, or a monosaccharide. In some embodiments, Y is a branched $C_4$ alkyl. In certain embodiments, Z is a hexose.

In certain embodiments, an antibiotic compound according to Formula I has a stereochemistry as shown in Formula II:

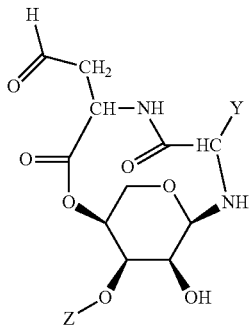

Formula II

In some embodiments, as shown in Formulas IIIA and IIIB, the antibiotic compound has a structure according to Formula I where Y is —$CH(CH_3)CH_2CH_3$.

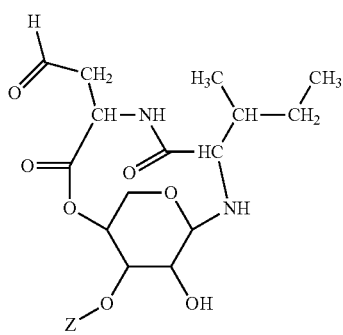

Formula IIIA

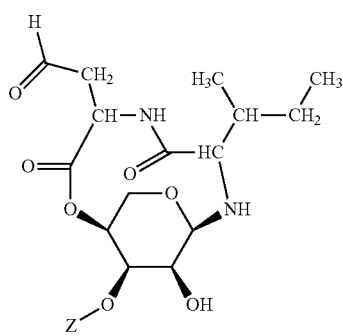

Formula IIIB

In another embodiment, as shown in Formula IV, the antibiotic compound has a structure according to Formula I where Y is —$CH(CH_3)CH_2CH_3$, and Z is xylose:

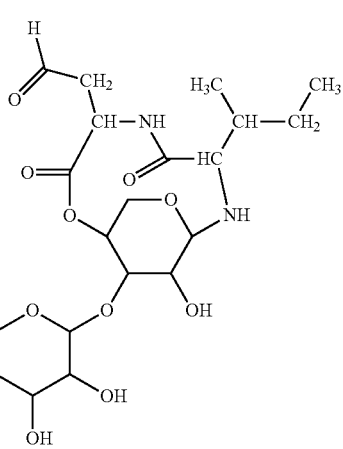

Formula IV

In a particular embodiment, the antibiotic compound has a structure according Formula III with a stereochemistry as shown below:

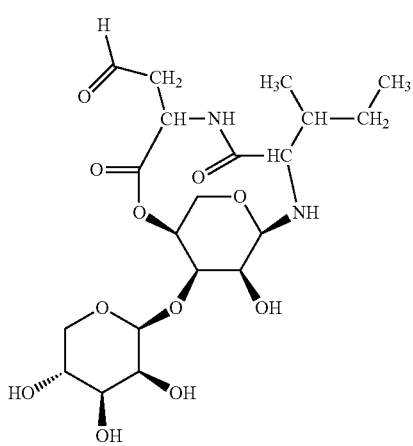

Compound #1

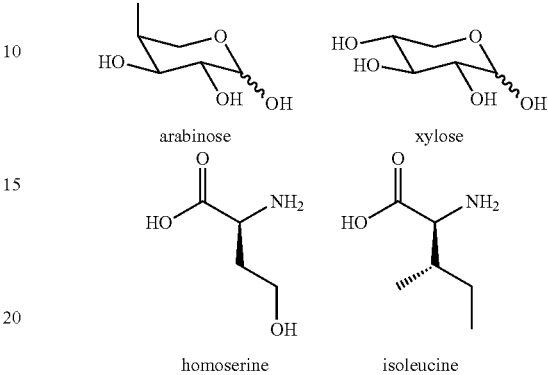

arabinose     xylose homoserine     isoleucine

In some embodiments, an antibiotic compound according to Formula I is isolated from a microorganism. For example, an antibiotic compound according to Formula I may be isolated from *Clostridium thermocellum, Herpetosiphon aurantiacus, Myxococcus xanthus, Streptosporangium roseum, Catenulispora acidiphila, Pyrobaculum aerophilum, Rickettsia conorii* or *Emericella nidulans*.

In certain embodiments, an antibiotic compound according Formula I is synthesized from its building blocks, which comprise one or two carbohydrate moieties and at least two amino acid moieties. In one embodiment, Compound #1 is synthesized from two carbohydrate moieties, xylose and arabinose, and two amino acid moieties, homoserine and isoleucine.

B. Synthesis

An exemplary synthesis of Compound #1 is shown in Scheme 1, wherein Compound #1 is synthesized from its starting blocks of xylose, arabinose, homoserine, and isoleucine:

Scheme 1

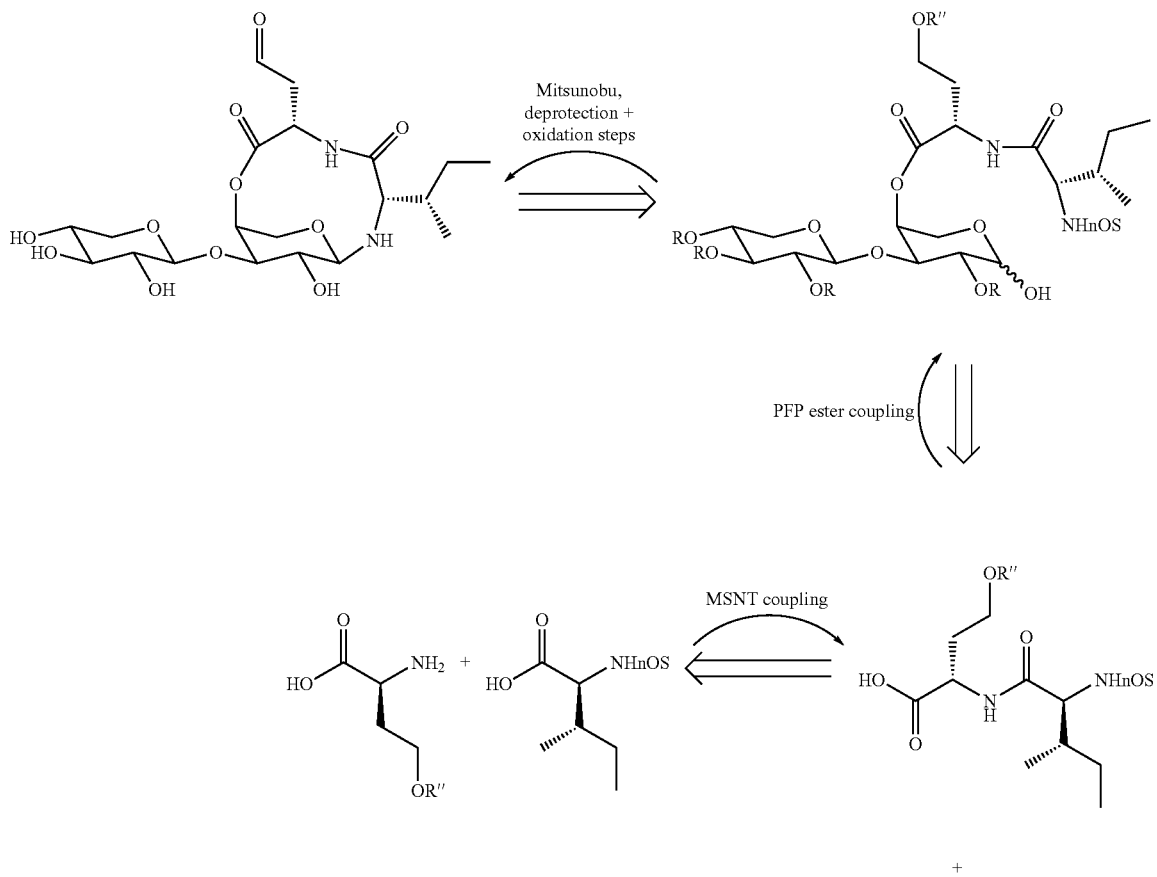

-continued

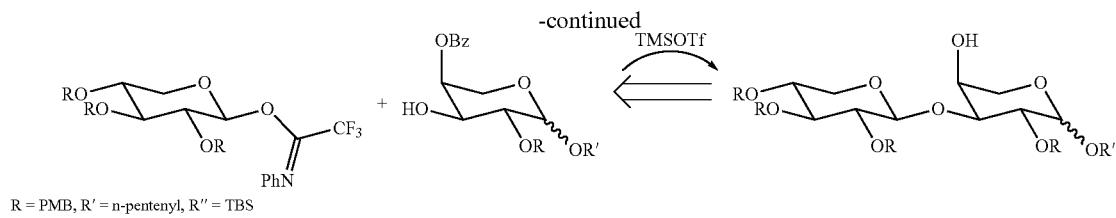

R = PMB, R' = n-pentenyl, R'' = TBS

In Scheme 1, PMB is p-methoxybenzyl ether, TBS is tert-butyldimethylsilyl ether, Bz is benzoyl, TMSOTf is trimethylsilyl trifluoromethanesulfonate, MSNT is 1-(mesitylene-2-sulfonyl)-3-nitro-1,2,4-triazole, and PFP ester is pentafluorophenyl ester.

Non-reacting hydroxyl groups of arabinose and xylose may be protected with protecting groups according to conventional methods known to one of ordinary skill in the art of organic synthesis. The side-chain hydroxyl group of homoserine, and the amino group of isoleucine also may be protected.

The two carbohydrate precursors may be coupled together via an intermolecular condensation reaction using TMSOTf. The two amino acid precursors may be coupled together via an intermolecular condensation reaction using MSNT. The carbohydrate dimer and amino acid dimer then may be joined in another intermolecular condensation reaction via PFP ester coupling. Finally, the amino acid dimer and the arabinose moiety may be cyclized via a Mitsunobu reaction, the protected homoserine hydroxyl group may be oxidized, and the remaining protective groups may be removed to produce Compound #1.

More generally, a compound according to Formula I is synthesized by providing a first amino acid having a formula Y—CH(NHnOS)C(O)OH, and a homoserine analog having the formula R"OCH$_2$CH$_2$CH(NH$_2$)C(O)OH. The first amino acid is coupled to the homoserine analog to form an amino acid dimer

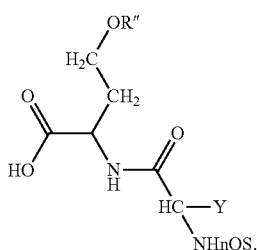

A carbohydrate precursor also is provided according to the structure:

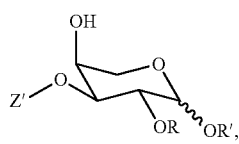

where Z' is hydrogen, R''' where R''' is a protecting group, or a monosaccharide precursor comprising one or more protecting groups in place of hydroxyl groups. The amino acid dimer is coupled to the carbohydrate precursor, forming the structure:

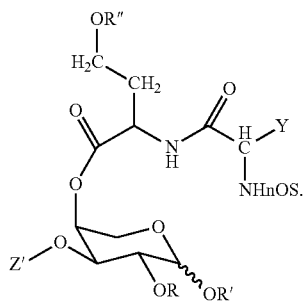

The amino acid dimer and carbohydrate precursor then are cyclized to form the structure:

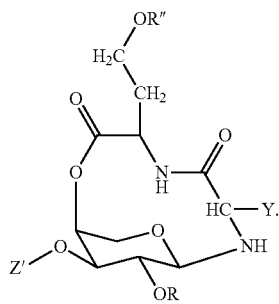

The protecting groups R and R'' are removed to form hydroxyl groups, and the hydroxyl group formed by removal of R'' is oxidized, thereby forming the compound according to Formula I.

In certain embodiments, Z is xylose, and providing the carbohydrate precursor includes providing first and second monosaccharide precursors having the structures:

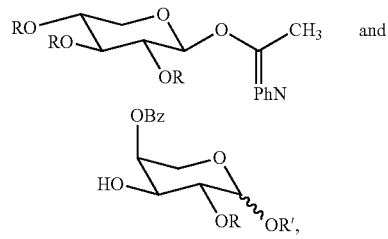

where R, R', and Bz are protecting groups p-methoxybenzyl ether, n-pentenyl, and benzoyl, respectively, and Ph is phenyl. The first and second monosaccharide precursors are coupled to form the carbohydrate precursor

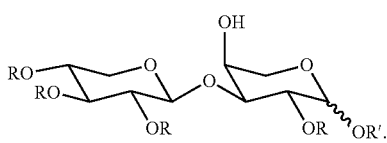

VII. Pharmaceutical Compositions and Administration Thereof

This disclosure includes pharmaceutical compositions comprising at least one antibiotic compound for use in human or veterinary medicine. Embodiments of pharmaceutical compositions include a pharmaceutically acceptable carrier and at least one active ingredient. Useful pharmaceutically acceptable carriers and excipients are known in the art. Active ingredients may comprise, for example, at least one antibiotic compound as described herein. In addition, other medicinal or pharmaceutical agents, for example, with similar, related or complementary effects on the affliction being treated, may be included as active ingredients in pharmaceutical compositions.

The pharmaceutical compositions comprising the antibiotic compounds disclosed herein may be formulated in a variety of ways depending, for example, on the mode of administration and/or on the location and type of infection to be treated. For example, such pharmaceutical compositions may be formulated as pharmaceutically acceptable salts. As another example, parenteral formulations may comprise injectable fluids that are pharmaceutically and physiologically acceptable fluid vehicles such as water, physiological saline, other balanced salt solutions, aqueous dextrose, glycerol or the like. Excipients may include, for example, non-ionic solubilizers, such as cremophor, or proteins, such as human serum albumin or plasma preparations. If desired, the pharmaceutical composition to be administered may also contain non-toxic auxiliary substances, such as wetting or emulsifying agents, preservatives, and pH buffering agents and the like, for example, sodium acetate or sorbitan monolaurate.

The dosage form of the pharmaceutical composition can be determined, at least in part, by the mode of administration chosen. For example, in addition to injectable fluids, topical and oral formulations may be employed. Topical preparations may include eye drops, ointments, sprays and the like. Oral formulations may be liquid (e.g., syrups, solutions or suspensions), or solid (e.g., powders, pills, tablets, or capsules). For solid compositions, conventional non-toxic solid carriers may include pharmaceutical grades of mannitol, lactose, starch, or magnesium stearate. Actual methods of preparing such dosage forms are known, or will be apparent, to those skilled in the art.

Certain embodiments of the pharmaceutical compositions comprising antibiotic compounds as described herein may be formulated in unit dosage form suitable for individual administration of precise dosages. The amount of a therapeutic compound administered will depend on the subject being treated, the type and severity of the infection, and the manner of administration, and is known to those skilled in the art. Within these bounds, the formulation to be administered will contain a quantity of the antibiotic compounds disclosed herein in an amount effective to achieve the desired effect in the subject being treated (e.g., reducing or eliminating Gram-positive pathogens or Gram-negative pathogens).

The present disclosure contemplates treatments for infection of a subject by Gram-positive bacteria, Gram-negative bacteria and/or Mycobacteria. Such treatments include administering an antibiotic compound disclosed herein, or a combination of the antibiotic compound and one or more other pharmaceutical agents, to the subject in a pharmaceutically acceptable carrier and in an amount effective to treat a microbial infection. Subjects can be selected using more specific criteria, such as a definitive diagnosis of a condition based on, for example, a biological specimen that has been provided to be tested for a bacterial infection.

The vehicle in which the antibiotic compound is delivered may include, for example, the pharmaceutical compositions described above. Routes of administration include but are not limited to oral and parenteral routes, such as intravenous, intraperitoneal, rectal, topical, ophthalmic, nasal, and transdermal.

Therapeutically effective doses of an antibiotic compound can be determined by one of skill in the art. An example of a dosage range is 0.1 to 200 mg/kg body weight orally in single or divided doses. Another example of a dosage range is 1.0 to 100 mg/kg body weight orally in single or divided doses. For oral administration, the compositions are, for example, provided in the form of a tablet containing 0.1 or 1.0 to 1000 mg of the active ingredient, particularly 1, 5, 10, 15, 20, 25, 50, 100, 200, 400, 500, 600, or 1000 mg of the active ingredient for the symptomatic adjustment of the dosage to the subject being treated.

The specific dose level and frequency of dosage for any particular subject may be varied and will depend upon a variety of factors, including the activity of the specific antibiotic compound, the metabolic stability and length of action of that compound, the age, body weight, general health, sex and diet of the subject, mode and time of administration, rate of excretion, drug combination, and type and severity of the infection in the subject being treated.

The following examples are provided to illustrate certain particular features and/or embodiments. These examples should not be construed to limit the disclosure to the particular features or embodiments described.

EXAMPLES

Example 1

Identification of a Non-Ribosomal Peptide Synthetase (NRPS) Gene Cluster in *Clostridium thermocellum* and Other Microorganisms This example describes the discovery of a non-ribosomal peptide synthetase (NRPS) cluster for the biosynthesis of a novel secondary metabolite in the sequenced genome of *Clostridium thermocellum*.

*C. thermocellum* (ATCC 27405) is a hyper-thermophilic anaerobic bacterial strain with an optimal growth temperature of 60° C. *C. thermocellum* is Gram-positive, rod-shaped, and produces endospores. This bacterium produces an extracellular enzyme system capable of degrading crystalline cellulose to soluble sugars. A new NRPS gene cluster was identified in the sequenced genome of *C. thermocellum*. The enzymatic functions of the encoded proteins of this natural product assembly line were identified (see FIG. 1 and FIG. 2). The assumed secondary metabolite appeared unusual since additional unique enzymatic functions are associated with its biosynthesis. These include two glycosyl-transferases with one active in the cytoplasm and the second one located in the periplasmic space. In addition, a copper amine-oxidase, responsible for a desamination reaction, was identified in the periplasm to be associated with the biosynthesis of this new natural product, referred to herein as Compound #1. The chemical structure of this small glyco-peptide was elucidated by NMR spectroscopy and mass spectrometry and its biosynthetic pathway was reconstructed in vitro by analyzing the order of the enzymatic functions associated with this NRPS cluster.

In addition to *C. thermocellum*, a number of additional strains were identified that carry genetic material in their genome coding for similar non-ribosomal peptide synthetase assembly systems. The identified strains are the following bacteria, archae bacterium and fungi:
  *Herpetosiphon aurantiacus* (ATCC 23779)
  *Myxococcus xanthus* DK 1622 (ATCC 19368/25232)
  *Streptosporangium roseum* DSM 43021 (ATCC 12428)
  *Catenulispora acidiphila* DSM 44928
  *Pyrobaculum aerophilum* (NCBI ID 13773)
  *Rickettsia conorii* (ATCC 613)
  *Emericella nidulans* (also known as *Aspergillus nidulans*) (ATCC 11267)

A second compound (Compound #2), produced by *Herpetosiphon aurantiacus* (ATCC 23779), was purified and the elucidated structure confirms the chemical structure of the first compound. In addition, a third compound produced by *Emericella nidulans* has been isolated and is referred to herein as Compound #3.

Example 2

Isolation and Characterization of an Antibiotic Compound Produced by the *C. thermocellum* NRPS Gene Cluster

Figure 3:
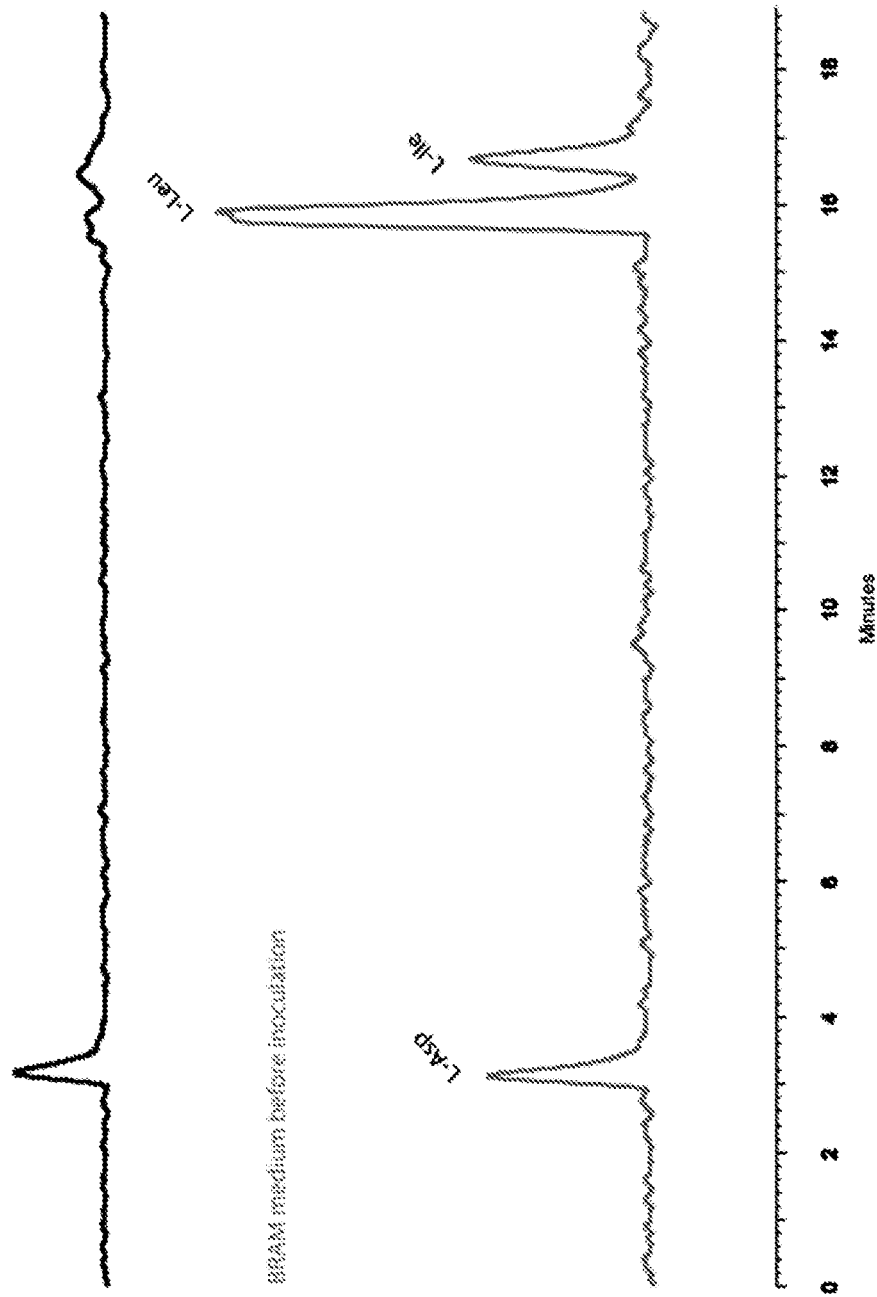
FIG. 3 shows the results of radio-high pressure liquid chromatography (HPLC) of a *C. thermocellum* culture containing $^{14}$C-labelled amino acids.
Figure 4:
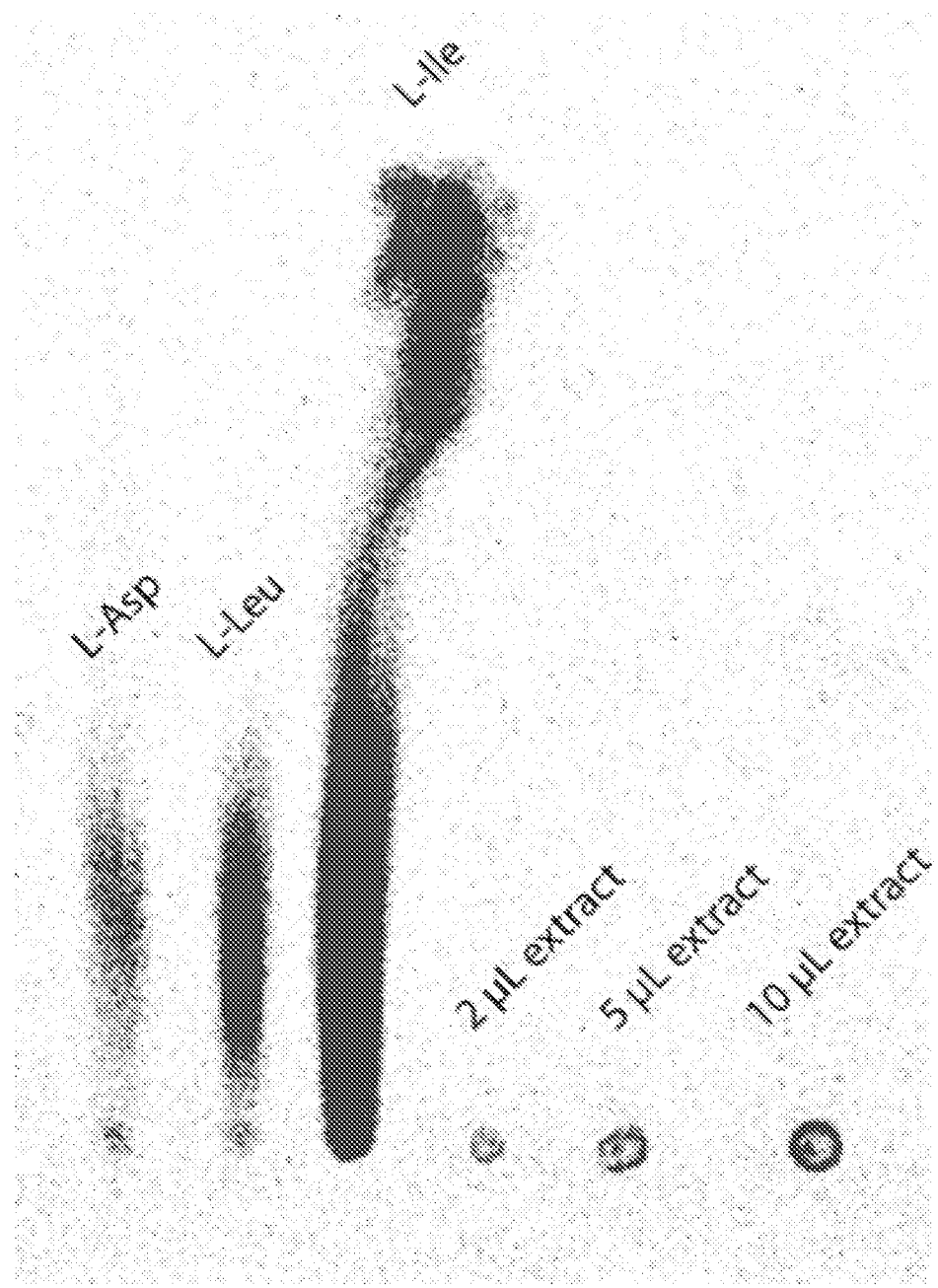
FIG. 4 is an image showing the results of thin layer chromatography (TLC) of a DMSO extract of the *C. thermocellum* secondary metabolite (Compound #1).

*C. thermocellum* was grown anaerobically in cellulose-containing medium. $^{14}$C-labelled amino acids ($^{14}$C-L-Asp, $^{14}$C-L-Leu and $^{14}$C-L-Ile) were added to the culture media and radio-HPLC was performed. The radiolabelled amino acids were consumed by *C. thermocellum* and no new peak was detected, indicating the secondary metabolite is water insoluble (FIG. 3). To extract the water insoluble pellet, a radiolabelled 2 L culture was filtered through a Büchner funnel, the solids were resuspended in 50 mL DMSO and shaken for 2 hours. The orange suspension was centrifuged, the liquid layer separated from the cells and the DMSO was removed under reduced pressure. The final yield from this process was 14.7 mg. Radio-thin layer chromatography (TLC) of 1 mg/mL solution in DMSO revealed an additional spot (FIG. 4).

Figure 5:
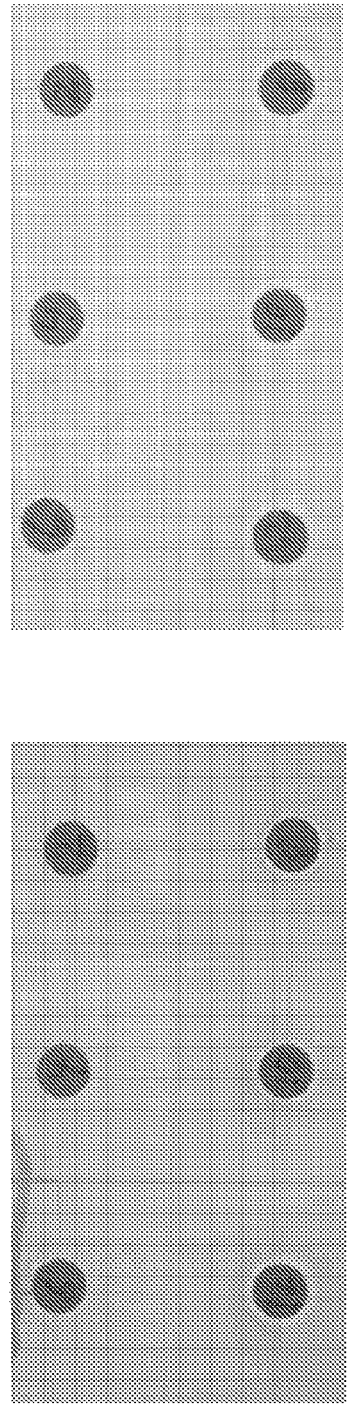
FIG. 5 shows the results of a disk diffusion assay to test the antibiotic properties of the DMSO extract of the *C. thermocellum* secondary metabolite. The DMSO extract was tested against *E. coli* and *B. subtilis* indicator strains.
Figure 5:
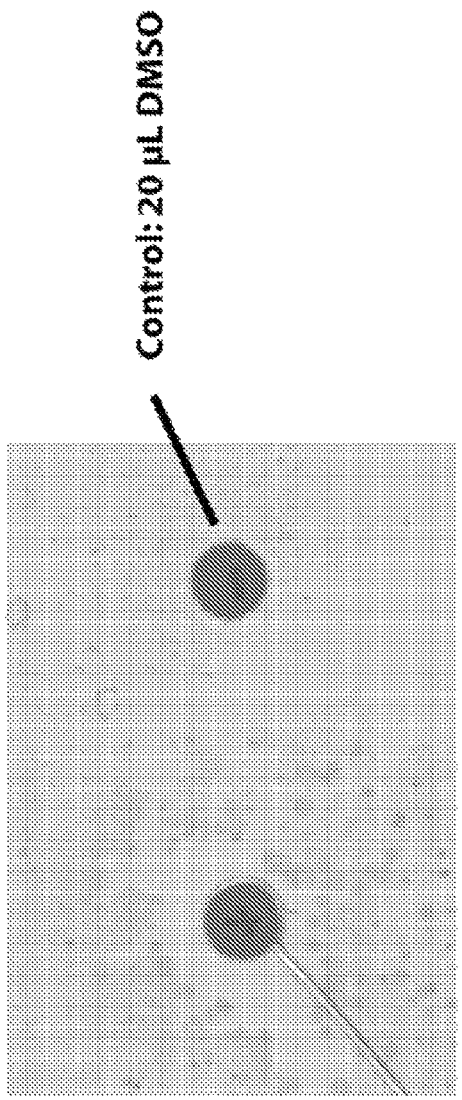

The DMSO extract of the solids was tested for antimicrobial activity against *E. coli* and *B. subtilis* indicator strains. As shown in FIG. 5, 20 μl of 1 mg/ml of the DMSO extract was bioactive against *B. subtilis*.

Cloning and Expression of *C. thermocellum* Genes

Genomic DNA was purchased from ATCC. PCR was carried out using Phusion HF Master Mix (Finnzymes). DNA was cloned into the pET151-DTOPO expression vector, which encodes for a hexa-His-tag and a TEV protease cleavage site. Genes (including Cthe-1904 A domain, Cthe_1905, Cthe_1906 and Cthe_1907) were expressed in BL21 Star™ (DE3) competent *E. coli* cells. Competent cells were grown at 37° C. until an OD of 0.6 was reached. Cells were induced with 0.1 mM IPTG final concentration, and further grown for 14 hours at 16° C. Protein was purified using Ni-NTA purification with increasing imidazole concentration.

Structure Elucidation by NMR

*C. thermocellum* cultures were fed $^{13}$C-glucose, which was incorporated into the secondary metabolite. The metabolite was isolated by DMSO extraction, as described above. For structure elucidation, 2D spectra were recorded ($^{13}$CHSQC, $^{13}$C refocused rotational NOESY, $^1$H$^1$H—COSY). The structure of Compound #1 contains a dipeptide, which is bridged by a sugar.

Growth of *C. thermocellum* Cultures

*C. thermocellum* can be grown in either small or large cultures, such as cultures of up to 5 gallons. A 5 gallons culture of *C. thermocellum* (ATCC 27405) usually grows for 18-24 days until sporulation has started. The production of the antibiotic secondary metabolite appears to be directly linked to sporulation and Compound #1 can be isolated by washing spores with di-methyl-sulfoxide (DMSO) and subsequently precipitated with ethanol and freeze dried to a DMSO solution. For each 5 gallon culture, approximately 85 mg of >95% pure compound is isolated and can be used for testing dissolved in 200 μl DMSO.

Example 3

NRPS Gene Cluster in *Herpetosiphon aurantiacus*

*Herpetosiphon aurantiacus* was originally isolated from Lake Birch in Minnesota in 1968. It is a Gram-negative bacterium which grows in long, flexible filaments with a transparent section of empty cell wall at the end of the filament. An NRPS gene cluster homologous to the one identified in *C. thermocellum* was found in *H. aurantiacus* (FIG. 6). 1D-$^1$H-NMR of the extract of the water-insoluble materials after centrifugation of the *H. aurantiacus* culture indicated a structure of the metabolite similar to Compound #1.

Genomic DNA of *H. aurantiacus* (ATCC 23779) was prepared and subject to PCR using Phusion HF Master Mix (Finnzymes). Amplified DNA was cloned into the pET151-DTOPO expression vector, which encodes for a hexa-His tag and a TEV protease cleavage site. Several *H. aurantiacus* genes (Haur_3126, Haur_3127, Haur_3128 and Haur_3129) were expressed in BL21 Star™ (DE3) competent *E. coli* cells. Competent cells were grown at 37° C. until an OD of 0.6 was reached. Cells were induced with 0.1 mM IPTG final concentration, and further grown for 14 hours at 16° C.

Example 4

Toxicity Screening of Antibiotic Compounds

In Vitro Assays

In vitro cell toxicology assays were performed to evaluate the effect of Compound #1 on human cells. Compound #1, dissolved in DMSO, was added to vital cultures of HeLa cells and peripheral blood mononuclear cells (PMBC) one day after the cell cultures were started. For each cell line, pure DMSO (control #1), no DMSO (control #2) and Compound #1 in one times (T1-5 nM), five times (T5-25 nM) and ten times (T10-50 nM) of the bacteria-toxic concentration was added to the cell cultures for two sets each. All ten culture flasks per cell line (2×: T1, T5, T10, C#1, C#2) were incubated under identical conditions and simple cell counts were performed on days two, four and six while replacing the cell culture medium to maintain the concentration of Compound #1.

The observed death rates for treated and untreated cell cultures were essentially identical (less than 5% variation). A slightly reduced proliferation rate for T10 (50 nM)-treated HeLa cells was observed in both experiments. No pyrogenic reactions, and no changes in physical appearance of either cell line, were observed.

Maximum Tolerated Dose (MTD) Studies

MTD studies were performed for Compound #1, Compound #2 and Compound #3. CD-1 mice, 6-8 weeks of age, were used for these studies. Groups of three mice were injected subcutaneously with 20 mg/kg, 40 mg/kg or 80 mg/kg of Compound #1, Compound #2 or Compound #3 Animals were observed 1 hour, 24 hours and 48 hours after administration of compound. No signs of illness were observed in the mice at any doses tested. These results indicate that all three compounds are well tolerated in vivo.

Example 5

Growth Inhibition and Minimum Inhibitory Concentration (MIC) Assays

To evaluate the antibiotic properties of the compounds produced by the NRPS cluster, Compound #1 or Compound #2 (0.85 µg) was diluted in 2 µl DMSO and soaked onto 6 mm cellulose disks for a bacterial growth inhibition assay. The results demonstrated that Compound #1 and Compound #2 significantly inhibited bacterial growth of the following Gram (+) and Gram(−) bacterial strains:

E. coli K-12

E. coli (ATCC 25922)

Staphylococcus aureus (ATCC 2913)

Pseudomonas putida (ATCC 11172)

Listeria grayi (ATCC 19120)

Acinetobacter baumannii (ATCC 17904)

Bacillus subtilis PY79

As a control, disks were soaked in DMSO alone. The control disks did not cause any bacterial growth inhibition.

Additional studies were carried out to determine the minimum inhibitory concentration (MIC) of Compound #1, Compound #2 and Compound #3 against *Pseudomonas aeruginosa*, *Salmonella enterica*, *Streptococcus pneumoniae*, *Haemophilus influenzae* and *Clostridium difficile*.

All compounds were completely dissolved in DMSO at a concentration of 25,600 µg/mL. Stocks of vancomycin hydrochloride (VAN) and ciprofloxacin (CIP) were prepared at a concentration of 3,200 µg/mL in water, and 400 µg/mL in slightly acidified water, respectively. Stocks of test compounds and standards were diluted 1:100 to provide working stocks in each growth medium.

For *P. aeruginosa*, *S. enterica* and *S. aureus*, eleven serial, one-half dilutions of the compounds and standards were prepared in 96-well polypropylene dilution blocks in cation-adjusted Mueller Hinton broth (CAMHB). The dilutions were transferred to 96-well assay plates. The assay concentration ranges of the test compounds were 128-0.12 µg/mL. Bacterial suspensions were prepared and added to each well at a concentration of approximately 5×10$^5$ colony-forming-units per milliliter. The inoculated plates were incubated for 16-20 hours at 35±1° C. At the completion of incubation the wells of each plate were evaluated visually for the presence of bacterial growth. The MIC was the concentration at which there was no growth.

MICs against *H. influenzae*, *S. pneumoniae* and *C. difficile* were determined similarly, but dilutions were prepared directly in the 96-well assay plates and MIC parameters were as indicated below (Table 1).

TABLE 1

MIC parameters (all incubations were at 35° C.)

| Species | Inoculum Medium | MIC Incubation Medium | Air | Incubation Time (h) |
|---|---|---|---|---|
| P. aeruginosa, S. enterica and S. aureus | Trypticase Soy Agar (TSA) | Cation Adjusted Mueller-Hinton Broth (CAMHB) | Ambient | 16-20 |
| S. pneumoniae | TSA + 5% Sheep's Blood (TSA + SB) | CAMHB + Lysed horse blood (LHB) | Ambient | 20-24 |
| H. influenzae | Chocolate Agar (enhanced $CO_2$) | Haemophilus Test Medium Broth | Ambient | 20-24 |
| C. difficile | TSA + SB (anaerobic) | Supplemented Brucella Broth + LHB | Anaerobic | 46-48 |

The standard for *H. influenzae*, *P. aeruginosa*, *S. enterica* and *S. aureus* was CIP (2-0.002 µg/mL); and the standard for *S. pneumoniae* and *C. difficile* was VAN (16-0.016 µg/mL). All testing was performed in duplicate.

Results

TABLE 2

Minimum inhibitory concentrations (MIC) of test compounds and standards against six species (µg/mL)

| | | Compound | | | Standard | |
|---|---|---|---|---|---|---|
| Species | ATCC[a] | #1 | #2 | #3 | CIP[b] | VAN[c] |
| P. aeruginosa | 27853 | >128 | >128 | >128 | 0.5[d] | — |
| S. enterica | 14028 | >128 | >128 | >128 | 0.25 | — |
| S. pneumoniae | 49619 | 64 | 16 | 64 | — | 0.25[e] |
| H. influenzae | 49247 | 2 | 1 | 2 | 0.016[f] | — |
| C. difficile | 700057 | 32 | 16 | 16 | — | 0.25 |

[a]American Type Culture Collection
[b]Ciprofloxacin
[c]Vancomycin hydrochloride
[d]CLSI acceptable range: 0.25-1 µg/mL
[e]CLSI acceptable range: 0.12-0.5 µg/mL
[f]CLSI acceptable range: 0.004-0.03 µg/mL The greatest activity observed was against the Gram-negative *H. influenzae*. Activity at high concentrations was also observed against the Gram-positive species *C. difficile* and *S. pneumoniae*.

MIC was further evaluated using EtOAc extracts of more highly purified Compound #1 and Compound #2. MIC of these compounds was compared to ACHN-490 (Plazomicin; an aminoglycoside effective primarily against Gram-negative bacteria), Colistin (a polymyxin antibiotic effective against most Gram-negative bacilli), and Meropenem (an ultra broad-spectrum, beta-lactam antibiotic). The results are shown in Table 3.

TABLE 3

MIC of Compounds #1 and #2 against seven bacterial species (μg/mL)

| Species | ATCC | Compound #1 | Compound #2 | ACHN-490 | Colistin | Meropenem |
|---|---|---|---|---|---|---|
| S. aureus (MRSA) | 33591 | 16 | 8 | 0.25 . . . 4 | 32 | >16 |
| S. enterica | 14028 | 16 | 8 | 0.25 . . . 4 | >32 | >16 |
| K. pneumoniae | 43816 | 8 | 4 | 0.25 . . . 64 | 0.12 | 0.5 . . . >16 |
| H. influenzae | 49247 | 0.5 | <0.125 | N/A | N/A | N/A |
| S. pneumoniae | 49619 | 16 | 8 | N/A | N/A | N/A |
| A. baumannii | 19606 | 8 | 4 | 8 | >32 | 1 |
| C. difficile | 70057 | 16 | 8 | N/A | N/A | N/A |

Both Compound #1 and Compound #2 exhibited antimicrobial activity against all bacterial strains tested.

Example 6

General Isolation Procedure for Purification of Antibiotic Secondary Metabolites Procedures for isolating antibiotic compounds produced by the NRPS gene clusters can vary depending upon, for example, the organism producing the secondary metabolite, the quantity of product desired and the solubility of the desired compound. The following procedure is a general procedure for isolation of the secondary metabolites. For solid cultures, such as spores of C. thermocellum or fungi cultures on plates, extractions of cells are performed using DMSO. Cultures are filtered and the clear DMSO extract is collected and washed with diethylether to remove fatty acids. The extract is precipitated and frozen (−20° C.) with ethanol to remove nucleic acids and proteins, then lyophilized to remove DMSO. The product is then washed with ethanol. The ethanol is removed to get a dry powder.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A compound according to Formula I:

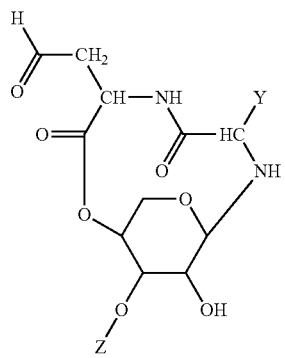

Formula I where Y is $C_1$-$C_{10}$ alkyl, and Z is hydrogen or a monosaccharide.

2. The compound of claim 1 where Y is a branched $C_4$ alkyl.

3. The compound of claim 2 where Y is —CH(CH$_3$)CH$_2$CH$_3$.

4. The compound of claim 1 where Z is a hexose.

5. The compound of claim 4 where Z is xylose.

6. The compound of claim 1 having the stereochemistry of Formula II:

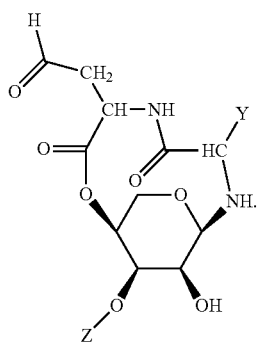

Formula II

7. The compound of claim 1 having the structure:

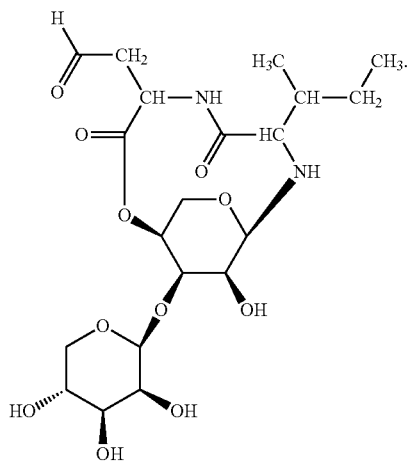 [SMILES: CCC(C)C1N[C@@H]2OC[C@H](OC(=O)C(CC=O)NC1=O)[C@H](O[C@@H]1OC[C@@H](O)[C@H](O)[C@@H]1O)[C@@H]2O]

8. A method of inhibiting bacterial growth, comprising contacting bacteria with the compound of claim 1.

9. The method of claim 8, wherein the bacteria are Gram-positive bacteria.

10. The method of claim 9, wherein the Gram-positive bacteria are selected from the group consisting of *Staphylococcus aureus, Streptococcus pneumoniae, Bacillus subtilis* and *Clostridium difficile*.

11. The method of claim 8, wherein the bacteria are Gram-negative bacteria.

12. The method of claim 11, wherein the Gram-negative bacteria are selected from the group consisting of *Pseudomonas aeruginosa, Salmonella enterica, Pseudomonas putida, Escherichia coli, Acinetobacter baumannii* and *Haemophilus influenzae*.

13. The method of claim 8, wherein the bacteria is a species of *Mycobacterium*.

14. The method of claim 13, wherein the *Mycobacterium* species is *Mycobacterium bovis* or *Mycobacterium tuberculosis*.

15. The method of claim 8, wherein the method is an in vitro method.

16. The method of claim 8, wherein the method is an in vivo method and contacting bacteria with the compound comprises administering a therapeutically effective amount of the compound to a subject infected with the bacteria.

17. The method of claim 16, wherein the subject is a non-human animal.

18. The method of claim 16, wherein the subject is a human.

19. A method of making a compound according to Formula I:

Formula I

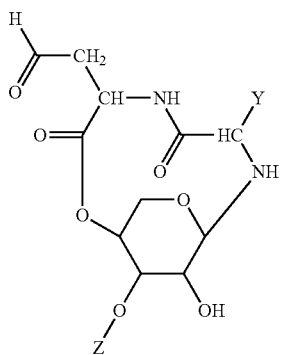

where Y is $C_1$-$C_{10}$ alkyl, and Z is hydrogen or a monosaccharide, the method comprising:

providing a first amino acid according to the formula Y—CH(NHnOS)C(O)OH, where nOS is a protecting group;

providing a homoserine analog according to the formula R"OCH$_2$CH$_2$CH(NH$_2$)C(O)OH where R" is a protecting group;

coupling the first amino acid to the homoserine analog to form an amino acid dimer;

providing a carbohydrate precursor having the structure

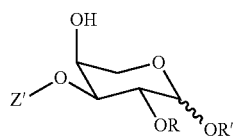

where R and R' are protecting groups, and Z' is hydrogen, R''' where R''' is a protecting group, or a monosaccharide precursor comprising one or more protecting groups in place of hydroxyl groups;

coupling the amino acid dimer to the carbohydrate precursor, thereby forming the structure

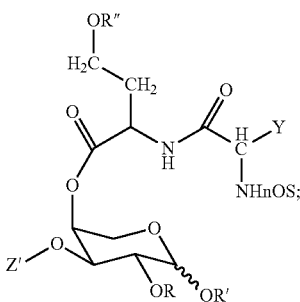

cyclizing the amino acid dimer and carbohydrate precursor, thereby forming the structure

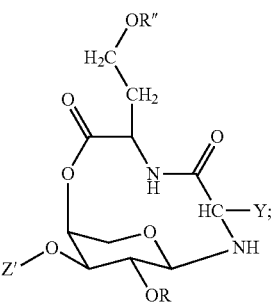

removing protecting groups to form hydroxyl groups, wherein the protecting groups comprise R, R" and, when Z' is R''', R'''; and oxidizing the hydroxyl group formed by removal of R", thereby forming the compound according to Formula I.

20. The method of claim 19, wherein the first amino acid and the homoserine analog are coupled via an intermolecular condensation reaction using 1-mesitylene-2-fulsonyl-3-nitro-1,2,4-triazole.

21. The method of claim 19, wherein the amino acid dimer is coupled to the carbohydrate precursor via pentafluorophenyl ester coupling.

22. The method of claim 19, wherein the amino acid dimer and carbohydrate precursor are cyclized via a Mitsunobu reaction.

23. The method of claim 19, wherein R is p-methoxybenzyl ether, R' is n-pentenyl, and R" is tert-butyldimethylsilyl ether.

24. The method of claim 19, wherein Z is xylose and providing the carbohydrate precursor further comprises:

providing first and second monosaccharide precursors having the structures

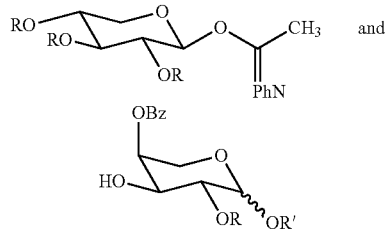

where R, R', and Bz are protecting groups p-methoxybenzyl ether, n-pentenyl, and benzoyl, respectively, and Ph is phenyl; and coupling the first and second monosaccharide precursors to form the carbohydrate precursor, wherein the carbohydrate precursor has the structure

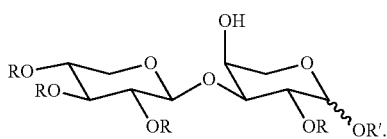

25. The method of 24, wherein the first and second monosaccharide precursors are coupled via an intermolecular condensation reaction using trimethylsilyl trifluoromethanesulfonate.

* * * * *

SEQUENCE LISTING

```
<160> NUMBER OF SEQ ID NOS: 6

<210> SEQ ID NO 1
<211> LENGTH: 1855
<212> TYPE: PRT
<213> ORGANISM: Clostridium thermocellum

<400> SEQUENCE: 1

Met Asn Leu Asn Ser Asn Ile Lys Glu Arg Ile Asn Gln Leu Pro Val
1               5                   10                  15

Glu Lys Arg Glu Leu Ile Met Gln Leu Leu Lys Lys Gln Asn Asn Lys
                20                  25                  30

Arg Glu Ile Gln Asn Glu Glu Asp Lys Ile Thr Leu Cys His Arg Glu
            35                  40                  45

Lys Gly Cys Ile Asn Tyr Phe Pro Leu Ser Tyr Phe Gln Gln Gly Leu
        50                  55                  60

Trp Phe Ile Asn Gln Leu Asp Pro Asn Asn Ser Ser Tyr Asn Ile Pro
65                  70                  75                  80

Leu Ala Tyr Arg Leu Val Gly Thr Leu Asn Lys Glu Ala Leu Lys Lys
                85                  90                  95

Ser Leu Glu Ile Ile Ile Asn Arg His Glu Val Leu Arg Thr Thr Phe
                100                 105                 110

Gln Glu Ile Asn Gly Glu Pro Phe Gln Val Ile Ser Pro Tyr Ser Lys
            115                 120                 125

Val Glu Leu Asn Ile Ile Asp Ile Ser His Ile Thr Gly Glu Asp Cys
        130                 135                 140

Glu Lys Leu Ala Leu Glu Ser Ala Arg Asn Glu Ala Asn Arg Leu Phe
145                 150                 155                 160

Asp Leu Thr Lys Gly Pro Leu Ile Arg Phe Leu Leu Ile Cys Lys Ser
                165                 170                 175
```

```
Gln Thr Glu His Ile Phe Val Val Thr Val His His Ile Ile Phe Asp
                180                 185                 190
Gly Trp Ser Thr Gly Ile Phe Cys Asn Glu Leu Ser Glu Ile Tyr Asn
            195                 200                 205
Ala Leu Ile Ser Gly Arg Glu Tyr Asn Leu Pro Gln Leu Glu Val Gln
        210                 215                 220
Tyr Ala Asp Tyr Val Val Trp Gln His Lys Lys Leu Asn Asn Glu Val
225                 230                 235                 240
Ile Glu Lys Gln Leu Thr Tyr Trp Arg Gln Lys Leu Thr Gly Asn Val
                245                 250                 255
Gln Val Ile Glu Leu Pro Thr Asp Arg Pro Arg Pro Ser Ile Lys Thr
            260                 265                 270
Val Arg Gly Gly Ala Leu Pro Phe Glu Leu Ser Pro Ala Leu Ser Lys
        275                 280                 285
Glu Ile Lys Ile Leu Thr Val Arg Lys Arg Cys Thr Leu Phe Met Thr
290                 295                 300
Leu Leu Ala Ala Phe Lys Thr Leu Leu Tyr Arg Tyr Thr Cys Gln Asp
305                 310                 315                 320
Asn Ile Thr Val Gly Thr Pro Ile Gly Asn Arg Ser Gln Leu Asp Cys
                325                 330                 335
Glu Lys Leu Met Gly Leu Phe Ile Asn Thr Leu Val Leu Cys Thr Lys
            340                 345                 350
Thr Gly Asp Asp Pro Ser Phe Ser Asp Leu Leu Glu Arg Val Arg Asn
        355                 360                 365
Val Thr Leu Glu Ala Tyr Glu Asn Gln Asp Ile Pro Phe Gln Lys Leu
    370                 375                 380
Val Glu Glu Leu Lys Pro Glu Arg Asp Leu Ser Arg Asn Val Phe Tyr
385                 390                 395                 400
Gln Val Met Phe Asn Phe Ser Asp Met Ser Lys Val Cys Met Arg Leu
                405                 410                 415
Glu Gly Leu Glu Val Ser Pro Phe Glu Leu Gly Gly Ser Thr Ala Asn
            420                 425                 430
Val Asp Leu Gln Leu Tyr Val Trp Gln Glu Gly Glu Val Ile Lys Gly
        435                 440                 445
Tyr Phe Glu Tyr Asn Lys Asp Leu Phe Asp Glu Ser Thr Ile Lys Arg
450                 455                 460
Leu Ile Glu Gln Tyr Lys Val Leu Leu Gln Gly Val Val Asn Asp Pro
465                 470                 475                 480
Glu Arg His Leu Ser Glu Leu Pro Ile Leu Pro Leu Glu Glu Lys Asn
                485                 490                 495
Lys Val Leu Tyr Glu Trp Asn Asp Asn Asp Val Ala Tyr Pro His Ile
            500                 505                 510
Asn Gly Leu His Lys Phe Phe Glu Arg Gln Val Glu Lys Thr Pro Asp
        515                 520                 525
Ser Pro Ala Val Phe Phe Glu Asn Glu Tyr Cys Thr Tyr Gln Glu Leu
    530                 535                 540
Asn Glu Arg Ala Asn Gln Leu Ala His Tyr Leu Ile Asn Ile Gly Ala
545                 550                 555                 560
Lys Lys Asn Thr Ala Ile Gly Leu Phe Leu Asp Arg Ser Ile Asp Met
                565                 570                 575
Ile Val Gly Met Phe Gly Ile Met Lys Ser Gly Ala Ala Tyr Val Pro
            580                 585                 590
Leu Asp Ile Lys Tyr Pro Ser Asp Arg Ile Ala Ala Ile Leu Lys Glu
```

-continued

```
            595                 600                 605
Ala Gly Ile Lys Ile Leu Ile Thr Gln Asp Leu Leu Ser Asp Val
            610                 615                 620
Pro Gln Met Glu Gly Leu Asn Val Ile Cys Ile Asp Arg Glu Gln Lys
625                 630                 635                 640
Lys Ile Cys Ser Phe Ser Lys Glu Asn Pro Ser Val Glu Val Ser Asn
                    645                 650                 655
Asn Asp Leu Leu Tyr Ile Leu Phe Thr Ser Gly Thr Thr Gly Lys Pro
                    660                 665                 670
Lys Gly Val Leu Val Glu His Arg Cys Tyr Ile Asn Tyr Ile Gln Gly
                    675                 680                 685
Ile Ile Arg Lys Leu Glu Ile Asp Ser Pro Leu Asn Phe Ala Ile Val
            690                 695                 700
Ser Ser Phe Ala Ala Asp Leu Gly Thr Thr Asn Ile Phe Ile Pro Leu
705                 710                 715                 720
Phe Thr Gly Gly Gln Leu His Ile Leu Ser Tyr Glu Arg Ala Thr Asp
                    725                 730                 735
Pro Glu Lys Phe Leu Asp Tyr Phe Arg Lys His Lys Ile Asp Ala Met
                    740                 745                 750
Lys Leu Val Pro Ser His Phe Glu Ala Leu Lys Thr Val Gln Asn Phe
                    755                 760                 765
Glu Asp Ile Ile Pro Gly Lys Arg Leu Val Phe Ala Gly Glu Ala Cys
770                 775                 780
Ser Trp Glu Leu Ile Glu Glu Val Arg Arg Leu Asn Pro Ser Cys Met
785                 790                 795                 800
Ile Gln Asn His Tyr Gly Pro Thr Glu Thr Thr Val Ser Ala Leu Ala
                    805                 810                 815
Tyr Leu Val Pro Asp Glu Leu Pro Gln His Ala Gly Ser Val Val Pro
                    820                 825                 830
Ile Gly Arg Pro Leu Pro Asn Val Lys Ala Tyr Val Leu Asp Lys His
                    835                 840                 845
Arg Gln Pro Val Pro Ile Gly Val Val Gly Glu Leu Tyr Ile Gly Gly
            850                 855                 860
Ala Gly Val Ala Arg Gly Tyr Ile Asn Glu Pro Glu Met Thr Lys Gln
865                 870                 875                 880
Lys Phe Ile Pro Asn Pro Phe His Pro Gly Pro Ser Ser Tyr Met Tyr
                    885                 890                 895
Arg Thr Gly Asp Leu Val Arg Tyr Leu Pro Asp Gly Asn Ile Glu Phe
                    900                 905                 910
Leu Gly Arg Ile Asp Arg Gln Ile Lys Ile Arg Gly Tyr Arg Ile Asp
            915                 920                 925
Pro Glu Glu Ile Glu His Ala Ile Lys Glu His Ser Val Val Arg Asp
            930                 935                 940
Ala Val Val Thr Val Arg Gly Asn Ser Glu Lys Ser Asn Lys Leu Val
945                 950                 955                 960
Ala Tyr Leu Val Leu Asp Lys Lys Ala Glu Gly Asn Leu Asp Ile Ser
                    965                 970                 975
Glu Ile Arg Arg Tyr Leu Lys Lys Leu Pro Glu Tyr Met Arg Pro
                    980                 985                 990
Ser Ser Phe Thr Val Leu Asp Ser Ile Pro Leu Asn Thr Asn Gly Lys
            995                 1000                1005
Val Asp Tyr Lys Ser Leu Pro Glu Pro Ser Glu Asp Ile Ile Glu
    1010                1015                1020
```

-continued

```
Asp Asp Asn Tyr Val Ala Pro Arg Asn Glu Leu Glu Glu Lys Ile
    1025            1030                1035

Ala Ser Ile Trp Lys Glu Thr Leu Glu Ile Ser Arg Val Gly Ile
    1040            1045                1050

Asp Asp Asn Phe Phe Asp Leu Gly Gly Glu Ser Phe Lys Ala Met
    1055            1060                1065

Ser Val Val Arg Lys Ile Ser Pro Ser Leu Ser Val Ile Asp Leu
    1070            1075                1080

Phe Lys Tyr Pro Thr Ile Arg Glu Leu Ser Asp Tyr Ile Ser Asn
    1085            1090                1095

Lys Gln Lys Glu Glu Lys Arg Glu Ile Leu His Glu Leu Thr Lys
    1100            1105                1110

His Val Ser Lys Glu Lys Lys Gln Met Asn Leu Ile Cys Ile Pro
    1115            1120                1125

Tyr Gly Gly Gly Ser Ala Val Ala Tyr Gln Pro Leu Ala Asn Glu
    1130            1135                1140

Ile Pro Glu Asn Trp Ser Leu Tyr Ala Val Gln Ile Pro Gly Arg
    1145            1150                1155

Asp Phe Ser Arg Pro His Glu Lys Pro Glu Ser Leu Glu Lys Val
    1160            1165                1170

Ala Glu Met Cys Ile Ser Glu Ile Lys Glu Lys Val Thr Gly Pro
    1175            1180                1185

Ile Val Leu Tyr Gly Gln Cys Val Gly Gly Ala Leu Ala Ile Lys
    1190            1195                1200

Leu Ala Tyr Met Met Glu Glu Gln Gly Met Glu Leu Val Gly Val
    1205            1210                1215

Ile Glu Ala Gly Asn Phe Pro Ser Pro Arg Leu Pro Gly Lys Trp
    1220            1225                1230

Phe Glu Leu Trp Ser Lys Ile Phe Pro Arg Asp Arg Trp Ile Ser
    1235            1240                1245

Asn Arg Leu Tyr Lys Glu Ile Leu Lys Ser Ile Gly Ala Pro Ile
    1250            1255                1260

Gly Gly Ser Asn Asn Glu Ala Glu Gln Asp Phe Ile Ile Arg Ser
    1265            1270                1275

Leu Arg His Asp Ser Arg Glu Ala Glu Asp Tyr Tyr Thr Lys Met
    1280            1285                1290

Phe Ser Thr Glu Asn Leu Lys Lys Leu Lys Ala Pro Ile Thr Cys
    1295            1300                1305

Val Val Gly Glu Arg Asp Arg Thr Thr Glu Phe Tyr Gln Glu Arg
    1310            1315                1320

Tyr Lys Glu Trp Glu His Phe Ser Asn Cys Val Asn Leu Arg Val
    1325            1330                1335

Ile Glu Asn Ala Gly His Phe Phe Gln Lys His Gln Ala Asp Ile
    1340            1345                1350

Leu Ala Gln Ile Ile Val Asp Gln Val Glu Lys Trp Lys Asn Ile
    1355            1360                1365

Arg Ser Ser Glu Phe Val Glu Glu Ala Leu Glu Glu Thr Val Asp
    1370            1375                1380

Lys Lys Lys Val Lys Thr Ser Ile Phe Asp Lys Ala Asn Val Lys
    1385            1390                1395

Pro Ser Met Lys Leu Phe Leu Phe Ile Ala Leu Gly Gln Ile Val
    1400            1405                1410
```

```
Ser Met Phe Gly Thr Ser Leu Thr Gly Phe Ala Leu Gly Tyr Trp
    1415                1420                1425

Ile Tyr Lys Glu Thr Gly Ser Val Ser Tyr Tyr Thr Leu Ile Ser
    1430                1435                1440

Val Cys Thr Leu Leu Pro Asn Ile Leu Ile Ser Pro Ile Ala Gly
    1445                1450                1455

Ala Val Ala Asp Arg Trp Asp Arg Arg Lys Ile Met Ile Ile Ser
    1460                1465                1470

Asp Thr Phe Ala Ala Met Gly Thr Leu Ala Ile Ala Leu Leu Leu
    1475                1480                1485

Trp Ser Gly Arg Leu Glu Ile Trp His Ile Tyr Ile Ser Thr Thr
    1490                1495                1500

Ile Ser Ser Ile Ala Gly Ala Phe Gln Arg Pro Ala Phe Leu Ala
    1505                1510                1515

Ala Ile Ala Gln Ile Thr Pro Lys Gln Tyr Leu Gly Gln Ala Asn
    1520                1525                1530

Gly Ile Ala Gln Met Gly Ser Ala Ser Gly Ser Met Leu Ala Pro
    1535                1540                1545

Ile Ile Gly Gly Met Leu Ala Ser Ser Ile Asn Leu Tyr Gly Ile
    1550                1555                1560

Leu Leu Ile Asp Phe Ile Ser Phe Leu Phe Ser Val Val Pro Leu
    1565                1570                1575

Leu Leu Val Ala Phe Pro Asn Tyr Met Phe Lys Lys Arg Glu Glu
    1580                1585                1590

Pro Phe Ile Glu Glu Ile Lys Gly Gly Trp Asn Tyr Ile Ile Lys
    1595                1600                1605

Arg Lys Cys Leu Ile Ile Met Ile Gly Phe Phe Ile Val Thr Asn
    1610                1615                1620

Phe Phe Met Ser Leu Ser Thr Val Leu Val Thr Pro Val Val Leu
    1625                1630                1635

Ala Phe Ala Ser Val Glu Thr Met Gly Ile Val Thr Ser Ala Asn
    1640                1645                1650

Gly Phe Gly Leu Ile Val Gly Ser Ile Ile Met Ser Leu Trp Gly
    1655                1660                1665

Gly Thr Lys Arg Arg Ala Asp Gly Met Ile Gly Tyr Val Ile Leu
    1670                1675                1680

Ser Gly Ile Cys Leu Ile Leu Ile Gly Ile Arg Pro Ser Val Val
    1685                1690                1695

Leu Ala Thr Ile Gly Leu Phe Gly Phe Gly Leu Ser Ile Ala Phe
    1700                1705                1710

Ile Asp Thr His Trp Gln Ile Leu Ile Gln Ser Lys Val Gly Leu
    1715                1720                1725

Glu Leu Gln Ala Arg Val Phe Ser Ile Asn Glu Met Leu Ala Phe
    1730                1735                1740

Ile Met Arg Pro Leu Ala Phe Phe Leu Ala Gly Pro Leu Ser Asp
    1745                1750                1755

Lys Val Phe Glu Pro Phe Met Ala Gly Glu Gly Asn Leu Ala Thr
    1760                1765                1770

Lys Ile Ser Met Ile Ile Gly Ser Gly Glu Gly Arg Gly Met Gly
    1775                1780                1785

Leu Ile Leu Val Leu Ser Gly Ile Ile Leu Thr Ile Trp Gly Ile
    1790                1795                1800

Met Gly Phe Asn Tyr Arg Pro Leu Arg Phe Met Glu Asp Val Leu
```

-continued

```
                1805                1810                1815
Pro Asp Ala Ile Pro Asp Pro  Val Ile Leu Lys Asp  Lys Asn Lys
            1820                1825                1830

Ile Gln Glu Leu Ala Asp Met  Gln Leu Leu Lys Thr  Ile Gln Asn
            1835                1840                1845

Asp Arg Lys Arg Ala Lys Ile
            1850                1855

<210> SEQ ID NO 2
<211> LENGTH: 1816
<212> TYPE: PRT
<213> ORGANISM: Herpetosiphon aurantiacus

<400> SEQUENCE: 2

Met Thr Glu Val Ala Arg Gln Leu Glu Asp Leu Ser Pro Glu Arg Arg
1               5                   10                  15

Ala Leu Leu Ala Gln Arg Leu Arg Gln Arg Gln Ala Ala Lys Pro Val
            20                  25                  30

Pro Ser Ile Pro Ala Leu Ala Arg Ile Gly Glu His Pro Ala Phe Glu
        35                  40                  45

Leu Ser Phe Ala Gln Gln Arg Leu Trp Phe Leu Ser Gln Trp Gln Pro
    50                  55                  60

Glu Ser Ala Ala Tyr His Ile Pro Ala Thr Phe Ser Ile Ala Gly Glu
65                  70                  75                  80

Ile Asn Val Ser Val Leu Gln Thr Cys Leu Asp Lys Ile Ile Gln Arg
                85                  90                  95

His Glu Val Leu Arg Ser Thr Ile Glu Val Leu Asn Asp Gln Pro Met
            100                 105                 110

Gln Val Ile Gln Pro Phe Arg Ser Leu Asp Leu Glu Leu Val Asp Leu
        115                 120                 125

Arg Gly Leu Ser Asn Glu Gln Gln Ala Ser Gln Arg Gln Gln Gln Ile
    130                 135                 140

Glu Arg His Ser Gln Gln Pro Phe Asp Leu Ser Lys Asp Leu Met Leu
145                 150                 155                 160

Arg Gly Leu Leu Leu His Thr Ala Ala Asp His Ala Glu Leu Val Leu
                165                 170                 175

Thr Ile His His Ile Ala Cys Asp Gly Trp Ser Ile Gly Val Leu Leu
            180                 185                 190

Arg Glu Leu Gly Gln Leu Tyr Glu Ala Gly Leu Arg Gly Glu Gln Leu
        195                 200                 205

Glu Leu Pro Ala Leu Pro Ile Gln Tyr Ala Asp Phe Ala Val Trp His
    210                 215                 220

Lys Arg Tyr Val Leu Glu Gln Val Tyr Gln Gln His Leu Asn Phe Trp
225                 230                 235                 240

Gln Glu Gln Leu Ser Gly Thr Leu Pro Leu Leu Asn Leu Pro Thr Asp
                245                 250                 255

His Ala Arg Pro Ala Val Lys Arg Asp Leu Gly Ala Thr Val Glu Tyr
            260                 265                 270

His Leu Pro Trp Ser Leu Val Glu Ala Val Glu Arg Leu Ser Arg Gln
        275                 280                 285

Glu Arg Ala Thr Pro Phe Met Leu Phe Met Ala Ala Phe Gln Val Leu
    290                 295                 300

Leu Tyr Arg Tyr Ser Gly Gln Ser Asp Leu Ile Ile Gly Thr Pro Ile
305                 310                 315                 320
```

-continued

```
Ala Asn Arg Thr Arg Arg Glu Ile Glu Asn Leu Ile Gly Phe Phe Val
            325                 330                 335

Asn Thr Leu Pro Ile Arg Val Asn Leu Ala Gly Ser Pro Ser Phe Arg
        340                 345                 350

Ser Leu Ile Ala Gln Val Arg Gln Thr Ser Leu Ala Ala Phe Glu His
            355                 360                 365

Gln Asp Met Pro Leu Glu His Leu Ile Asp Val Leu Lys Val Glu Arg
        370                 375                 380

Ser Leu Ser His Asn Pro Leu Phe Gln Ala Leu Phe Val His Gln Thr
385                 390                 395                 400

Thr Ser Ile Gln Thr Val Asp Ser Gly Glu Phe Gly Leu Gln Phe Gly
            405                 410                 415

Gly Ala Ile Glu Thr Gly Ser Ala Lys Phe Asp Ile Asn Leu Asn Leu
        420                 425                 430

Ala Ala Asn Arg Ala Thr Phe Glu Tyr Asn Thr Asp Leu Phe Glu Arg
        435                 440                 445

Ser Thr Ile Glu Arg Met Ala Ser His Phe His Ser Leu Leu Glu Tyr
        450                 455                 460

Ala Val Thr Asn Pro Asp Ala Ser Ile Glu His Leu Pro Leu Leu Ser
465                 470                 475                 480

Ser Ser Glu Arg Gln Gln Leu Leu Gln Thr Trp Asn Ser Thr Ser Ala
            485                 490                 495

Asn Tyr Pro Ala Val Asp Ser Ile Val Arg Leu Phe Glu Ala Gln Ala
        500                 505                 510

Ala Arg Val Pro Glu Arg Thr Ala Leu His Phe Glu Gly Gln Thr Leu
        515                 520                 525

Ser Tyr Ala Glu Leu Asn Gln Arg Ala Asn Gln Leu Ala His Ser Leu
        530                 535                 540

Arg Gln Arg Gly Ile Gly Cys Asp Met Arg Val Gly Leu Phe Ile Asp
545                 550                 555                 560

Arg Ser Leu Asp Leu Leu Val Gly Ala Leu Gly Ile Leu Lys Ala Gly
            565                 570                 575

Ala Ala Tyr Val Pro Ile Asp Pro Ile Tyr Pro Gln Asp Arg Ile Ser
        580                 585                 590

Ala Met Leu Glu Asp Gly Ala Val Ser Leu Leu Thr His Ala Glu
        595                 600                 605

Leu Ala Ala Glu Leu Pro Lys Leu Asp Leu Glu Val Leu Cys Leu Asp
        610                 615                 620

Gln Ala Trp Pro Thr Ile Ala Gln Ala Pro Thr His Asn Leu Asn Leu
625                 630                 635                 640

Ala Leu Glu Pro Arg Ser Leu Met Tyr Val Leu Phe Thr Ser Gly Ser
            645                 650                 655

Thr Gly Arg Pro Lys Gly Val Ala Ile Glu His His Asn Tyr Val Asn
        660                 665                 670

Tyr Ile Gln Gly Leu Leu Gln Arg Ile Glu Ala Glu Asp Gly Trp Ser
        675                 680                 685

Tyr Ala Leu Val Ser Thr Phe Ala Ala Asp Leu Gly Thr Thr Asn Val
        690                 695                 700

Tyr Gly Ala Leu Cys Ser Gly Gly Glu Leu His Ile Val Ala Tyr Glu
705                 710                 715                 720

Arg Ala Thr Asp Pro Glu Ala Phe Ala Ala Tyr Phe Arg Gln His Arg
            725                 730                 735

Ile Asp Val Met Lys Leu Val Pro Ser His Phe Glu Ala Met Arg Gly
```

```
                740             745             750
Leu Asn Asn Leu Ala Asp Val Ile Pro Lys Gln Arg Leu Ile Leu Ala
        755             760             765
Gly Glu Ala Ser Leu Trp Glu Gln Leu Ser Asp Ile Arg Gln Leu Gln
        770             775             780
Pro Ser Val Gln Leu Gln Asn His Tyr Gly Pro Thr Glu Thr Thr Val
785             790             795             800
Ser Met Leu Thr Tyr Pro Ile Pro Ser Gln Pro His Tyr Pro Ser Ser
            805             810             815
Thr Val Pro Leu Gly Arg Pro Leu Gly Asn Val Gln Ile Tyr Val Leu
            820             825             830
Asp Arg Arg Met Gln Pro Thr Pro Gln Gly Val Pro Gly Glu Leu Tyr
            835             840             845
Val Gly Gly Ala Gly Val Gly Arg Gly Tyr Ile Gly Arg Pro Asp Leu
        850             855             860
Thr Ala Glu Arg Phe Val Pro Asn Pro Phe Ser Thr Glu Ala Gly Ala
865             870             875             880
Arg Leu Tyr Arg Ser Gly Asp Leu Val Arg Tyr Gln Pro Asp Gly Ala
            885             890             895
Ile Glu Phe Leu Gly Arg Ile Asp Leu Gln Val Lys Ile Arg Gly Tyr
        900             905             910
Arg Val Glu Leu Ser Glu Ile Glu Thr Ala Ile Gln Ala Gln Ala Gln
        915             920             925
Val Ala Asn Ser Val Val Ile Leu Arg Glu Asp Thr Pro Gly Asp Lys
        930             935             940
Arg Leu Val Ala Tyr Ile Val Pro Glu Ala Gly Gln Ser Leu Asn Ile
945             950             955             960
Gly Ser Ile Arg Glu Ala Leu Arg Asn Ser Leu Pro Asp Tyr Met Val
            965             970             975
Pro Thr Ala Phe Val Glu Leu Asp Gly Leu Pro Leu Asn Pro Asn Gly
            980             985             990
Lys Ile Glu Arg Arg Ala Leu Pro Ala Pro Ser Asn Glu Arg Asn Leu
        995             1000            1005
Asp Ser Tyr Val Ala Pro Gln Thr Ala Thr Glu His Glu Leu Ala
    1010            1015            1020
Gly Ile Trp Ala Glu Val Leu Gly Leu Asp Gln Val Gly Ile Asp
    1025            1030            1035
Asp Asn Phe Phe Asp Leu Gly Gly Glu Ser Phe Lys Ala Ile Arg
    1040            1045            1050
Val Val Arg Lys Ile Gly Ser His Ile Ser Val Met Thr Leu Phe
    1055            1060            1065
Lys Tyr Pro Thr Val Arg Glu Leu Ala Ala His Leu Ser Gly Ala
    1070            1075            1080
Ser Ser Ala Glu Ser Gly Gly Met Leu Tyr Glu Leu Ser Lys Ala
    1085            1090            1095
Gln Ala Lys Gln His Thr Thr Ile Val Ala Ile Pro Tyr Gly Gly
    1100            1105            1110
Gly Ser Ala Ile Thr Tyr Gln Pro Leu Ala Gln Ala Met Pro Lys
    1115            1120            1125
Gly Tyr Arg Leu Leu Ala Ala Glu Leu Pro Gly His Asp Phe Ser
    1130            1135            1140
Arg Pro Asp Glu Pro Leu Gln Ala Leu Glu Val Val Ala Ser Gln
    1145            1150            1155
```

```
Leu Ala Ser Glu Ile Gln Thr Lys Thr Gln Gly Pro Ile Val Leu
    1160                1165            1170

Tyr Gly His Cys Val Gly Ser Ala Met Thr Val Glu Ile Gly Arg
    1175                1180            1185

Leu Leu Glu Gln Ala Gly Arg Asp Val Gln Gly Ile Val Leu Gly
    1190                1195            1200

Gly Asn Phe Pro Ala Ala Arg Val Pro Gly Arg Phe Phe Glu Trp
    1205                1210            1215

Leu Asn Lys Leu Met Pro Ala Asp Arg Trp Met Ser Asp Arg Thr
    1220                1225            1230

Tyr Arg Asp Phe Leu Arg Ala Leu Gly Gly Phe Thr Glu Ile Val
    1235                1240            1245

Asp Gln Ala Glu Gln Thr Phe Val Met Arg Ser Leu Arg His Asp
    1250                1255            1260

Ala Arg Glu Val Glu Arg Tyr Phe Thr Gln Ala Phe Ala Gln Lys
    1265                1270            1275

Gln Ser Gln Gln Leu Lys Ala Pro Ile Ala Cys Ile Ile Gly Glu
    1280                1285            1290

Met Asp Arg Ala Thr Glu Tyr Tyr Gln Glu Arg Tyr Arg Glu Trp
    1295                1300            1305

Glu Tyr Phe Ser Asn Asn Val Thr Leu His Val Ile Pro His Ala
    1310                1315            1320

Gly His Tyr Phe Leu Lys His Gln Ala Ser Glu Leu Gly Gln Ile
    1325                1330            1335

Ile Glu Gln Gln Thr Glu Gln Trp Gln Pro Arg Pro Ile Gln
    1340                1345            1350

Pro Thr Ala Ala Lys Ser Lys Ser His Lys Thr Ser Met Pro Ser
    1355                1360            1365

Leu Arg Ile Phe Phe Met Val Ala Leu Gly Gln Leu Val Ser Met
    1370                1375            1380

Leu Gly Ser Ser Leu Ser Ser Phe Ala Leu Gly Ile Trp Ile Tyr
    1385                1390            1395

Gln Arg Thr Gly Thr Val Ser Asp Phe Ala Phe Thr Ala Ile Ala
    1400                1405            1410

Ser Met Leu Pro Ser Leu Leu Val Ser Pro Leu Ala Gly Ala Ile
    1415                1420            1425

Ala Asp Arg Trp Asp Arg Arg Trp Ile Met Ile Ile Ala Asp Thr
    1430                1435            1440

Ile Ser Ala Leu Ser Thr Ile Val Ile Ala Met Leu Leu Trp Ala
    1445                1450            1455

Asn Lys Leu Glu Val Trp His Ile Tyr Leu Thr Ala Ala Ile Ser
    1460                1465            1470

Ser Ile Ala Gly Thr Phe Gln Arg Pro Ala Tyr Ala Ala Ala Met
    1475                1480            1485

Thr Gln Leu Val Pro Lys Gln Tyr Leu Gly His Ala Asn Gly Val
    1490                1495            1500

Ile Gln Leu Gly Ser Ala Thr Gly Gly Leu Ile Ala Pro Phe Ile
    1505                1510            1515

Ala Gly Gly Met Val Ala Phe Phe Gly Leu Gly Gly Val Phe Leu
    1520                1525            1530

Leu Asp Phe Ile Ser Phe Ser Leu Gly Ile Gly Val Leu Phe Leu
    1535                1540            1545
```

-continued

```
Val Arg Phe Pro Asn Thr Leu Tyr His Lys Arg Glu Glu Pro Leu
1550                1555                1560

Leu Arg Glu Ile Val Arg Gly Trp Glu Tyr Ile Ile Lys Arg Pro
1565                1570                1575

Ser Leu Val Ala Met Val Leu Phe Phe Ala Leu Gly Asn Ile Trp
1580                1585                1590

Phe Gly Ile Ala Ser Ile Ser Met Ser Pro Leu Val Leu Ser Phe
1595                1600                1605

Gly Gly Pro Ala Glu Leu Gly Ile Val Ser Ala Ala Cys Ala Leu
1610                1615                1620

Gly Gly Phe Leu Gly Gly Leu Phe Met Ser Leu Trp Gly Gly Leu
1625                1630                1635

Gln Arg Arg Ala Glu Gly Met Val Gly Phe Val Ile Leu Glu Gly
1640                1645                1650

Phe Phe Ile Ala Leu Ala Gly Leu Arg Pro Ser Val Trp Leu Val
1655                1660                1665

Ala Leu Ala Met Phe Gly Met Trp Phe Ala Ile Ser Leu Val Asn
1670                1675                1680

Ala His Trp Gln Val Leu Ile Gln Thr Lys Val Gly Leu Glu Leu
1685                1690                1695

Gln Gly Arg Val Gln Ala Thr Asn Gln Met Leu Ala Met Leu Ser
1700                1705                1710

Ile Pro Leu Gly Tyr Trp Leu Ala Gly Pro Leu Ala Asp Asn Leu
1715                1720                1725

Phe Gly Pro Leu Leu Glu Pro Asn Gly Ala Leu Ser Ser Ser Leu
1730                1735                1740

Gly Trp Leu Phe Gly Val Gly Pro Asp Arg Gly Ile Gly Leu Leu
1745                1750                1755

Met Val Val Val Gly Leu Gly Ala Ala Ile Trp Ala Leu Ile Gly
1760                1765                1770

Phe Asn Tyr Arg Pro Leu Arg Tyr Met Glu Asp Ala Leu Pro Asp
1775                1780                1785

Ala Ile Pro Asp Ala Glu Ile Ala Ser Asp Arg Asp Thr Ile Gln
1790                1795                1800

Ala Gln Ala Asp Gly Ile Ile Ala Val Thr Ala Lys Gly
1805                1810                1815
```

<210> SEQ ID NO 3
<211> LENGTH: 2720
<212> TYPE: PRT
<213> ORGANISM: Streptosporangium roseum

<400> SEQUENCE: 3

```
Met Thr Glu Val Arg Gln Asp Arg Ile Ala Glu Met Val Arg Ser Arg
1               5                   10                  15

Phe Ala Ala Ala Arg Val Ala Ala Glu Thr Pro Gly Ala Ala Val Ile
                20                  25                  30

Pro Ala Leu Ser Thr Leu Asp Met Pro Leu Ser Pro Ala Gln Glu Arg
        35                  40                  45

Leu Trp Phe Leu Ala Gln Leu Glu Gln Asp Thr Pro Ala Tyr Asn Val
    50                  55                  60

Pro Arg Ala Leu Arg Leu Ser Gly Pro Val Asp Val Ala Ala Leu Thr
65                  70                  75                  80

Ala Ala Val Ser Glu Leu Ala Asp Arg His Trp Ile Leu Arg Gly Val
                85                  90                  95
```

```
Ile Asp Gly Ala Arg Val Arg Pro Ala Asp Gly Val Pro Val Ser Val
            100                 105                 110

Val Asp Val Asp Pro Ala Ala Leu Glu Arg Glu Leu Ala Glu His Ala
            115                 120                 125

Trp Arg Pro Phe Arg Leu Asp Ala Glu Pro Pro Met Arg Ala Ala Val
            130                 135                 140

Phe Arg Leu Gly Glu Asp Glu Tyr Val Leu Ala Leu Thr Leu His His
145                 150                 155                 160

Ile Ala Thr Asp Ala Trp Ser Glu Gln Leu Leu Arg Asp Leu Ser
                165                 170                 175

Ala Leu Tyr Ala Ala Arg Leu Gly Leu Ala Pro Gln Pro Glu Pro Pro
            180                 185                 190

Ala Leu Gln Tyr Ala Asp Val Ala Ala Trp Glu Ala Glu Gln Pro Glu
            195                 200                 205

Val Asp Leu Asp Trp Trp Thr Gln Arg Leu Ala Gly Leu Pro Pro Val
            210                 215                 220

Leu Asp Leu Pro Ile Ala Gly Pro Arg Pro Ala Val Pro Thr Trp Arg
225                 230                 235                 240

Gly Ala Ala Val Gly Phe Glu Val Pro Glu Ser Leu Ser Ser Lys Val
                245                 250                 255

Arg Ala Val Ala Gly Met Thr Pro Phe Met Val Phe Leu Ala Gly Leu
            260                 265                 270

Gln Ala Leu Leu Ser Arg Leu Ser Gly Ser Asp Asp Ile Ala Val Gly
            275                 280                 285

Val Pro His Ala Gly Arg His His Leu Asp Ala Glu Arg Val Val Gly
            290                 295                 300

Cys Phe Ile Asn Thr Leu Ala Val Arg Thr Asp Thr Ser Gly Asp Pro
305                 310                 315                 320

Thr Gly Ala Glu Leu Leu Ser Arg Ala Arg Thr Ala Ala Leu Asp Ala
                325                 330                 335

Phe Thr His Ala Arg Thr Pro Phe Glu Arg Ile Val Glu Arg Leu Gln
            340                 345                 350

Pro Glu Arg Asn Leu Ser Val Thr Pro Leu Phe Gln Val Met Leu Asn
            355                 360                 365

Val Tyr Asp Ala Ala Ala Pro Val Ser Leu Ala Gly Val Glu Val Arg
            370                 375                 380

Ala Glu Pro Leu Pro Val Pro Thr Ala Lys Phe Asp Leu Asn Leu Thr
385                 390                 395                 400

Leu Gly Asp Glu Gly Asp Arg Phe Ala Gly Glu Leu Arg Tyr Arg Ala
                405                 410                 415

Asp Leu Phe Glu Glu Ser Thr Val Arg Arg Leu Val Glu Trp Tyr Leu
            420                 425                 430

Ala Leu Leu Glu Gly Met Leu Thr Asp Pro Asp Ala Pro Val Arg Leu
            435                 440                 445

Pro Ala Gly Ala Asp Leu Arg Gly Pro Ala Gly Asp Leu Pro Thr Asp
            450                 455                 460

Val Pro Leu His Ala Leu Val Glu Arg Met Ala Asp Ala Gly Pro Asp
465                 470                 475                 480

Val Thr Ala Val Ala Ser Leu Ser Tyr Ala Glu Leu Asp Arg Arg Ala
                485                 490                 495

Asn Gln Val Ala His Trp Leu Leu Ala Arg Gly Val Gly Pro Gln Glu
            500                 505                 510
```

```
Pro Val Gly Val Leu Leu Glu Arg Arg Pro Glu Leu Val Ala Leu
            515                 520                 525

Leu Gly Val Leu Lys Ala Gly Ala Ala Tyr Leu Pro Leu Asp Pro Val
        530                 535                 540

Tyr Pro Ala Arg Arg Thr Glu Ala Ile Leu Ala Asp Ala Gly Ala Arg
545                 550                 555                 560

Ile Val Leu Thr Glu Ser Glu Ile Ala Ala Ala Asp Gly Pro Gly
                565                 570                 575

His Arg Pro Asp Val Ala Val Arg Pro Asp His Leu Ala Tyr Val Ile
            580                 585                 590

Tyr Thr Ser Gly Ser Thr Gly Glu Pro Lys Gly Val Ala Val Glu His
        595                 600                 605

Arg Gln Ile Thr His Tyr Leu Gly Ala Val Ala Glu Arg Ile Pro Ala
    610                 615                 620

Gly Val Thr Ser Phe Ala Leu Val Ser Thr Ala Ala Ala Asp Leu Gly
625                 630                 635                 640

Leu Thr Asn Val Leu Cys Ala Leu Thr Ser Gly Ala Thr Leu His Leu
                645                 650                 655

Ile Asp His Glu Thr Ala Thr Asp Pro Val Ala Tyr Ala Ala Tyr Met
            660                 665                 670

Ala Ala His Pro Val Asp Val Ile Lys Met Val Pro Ser Gln Leu Glu
        675                 680                 685

Leu Leu Gly Val Asp Ala Leu Pro Arg Lys Leu Leu Ile Leu Ala Gly
    690                 695                 700

Glu Ala Val Pro Ser Asp Leu Val Glu Arg Val Arg Ala Ala Arg Pro
705                 710                 715                 720

Ala Leu Ala Val Gln Ile His Tyr Gly Pro Thr Glu Thr Thr Val Ser
                725                 730                 735

Val Leu Ala Cys Asp Ala Ala Glu Val Ala Pro Gly Val Ala Pro Leu
            740                 745                 750

Gly Arg Pro Leu Ala Asp Val Glu Cys Arg Val Val Asp Ser Ala Gly
        755                 760                 765

Arg Pro Leu Pro Ala Gly Val Pro Gly Glu Leu Trp Ile Gly Gly Pro
    770                 775                 780

Ser Leu Ala Arg Gly Tyr Leu Gly Arg Pro Asp Leu Thr Ala Gln Arg
785                 790                 795                 800

Phe Val Asp Gly Trp Tyr Arg Thr Gly Asp Arg Val Arg Val Asn Pro
                805                 810                 815

Ala Gly Leu Val Glu Phe Leu Gly Arg Ile Asp Asp Gln Val Lys Val
            820                 825                 830

Arg Gly Phe Arg Val Glu Leu Gly Glu Val Ala Ala Leu Arg Ala
        835                 840                 845

Leu Pro Gln Val Ala Glu Ala Phe Val Gln Pro Val Gly Ala Gly Ala
    850                 855                 860

Gln Arg Arg Leu Ala Ala Trp Val Thr Pro Ser Thr Val Asp Thr Ala
865                 870                 875                 880

Gln Val Arg Ala Thr Leu Arg Glu Arg Leu Pro Asp Tyr Met Val Pro
                885                 890                 895

Pro Ala Ile Ala Ala Leu Glu Ala Leu Pro Thr Pro Asn Gly Lys
            900                 905                 910

Val Asp Arg Ala Ala Leu Pro Val Pro Glu Ala Gly Ser Ala Val Arg
        915                 920                 925

Val Pro Leu Gly Thr Pro Gln Glu His Leu Val Ala Glu Val Trp Ala
```

```
                930             935             940
Glu Val Leu Asp Leu Pro Gln Val Trp Ala Asp Asp Phe Phe Ala
945                 950             955                 960

Leu Gly Gly His Ser Phe Ala Ala Thr Arg Ala Val Gly Arg Leu Arg
                965             970             975

Glu Arg Leu Gly Ala Pro Val Pro Val Arg Leu Leu Phe Glu His Pro
            980             985             990

Val Leu Ala Asp Leu Ala Ala Ala  Leu Pro Arg Pro Val Gln Val Val
        995             1000            1005

Arg Ala  Arg Arg Glu Arg Ala  Asp Gly Pro Ala Ala  Leu Ser Gly
    1010             1015            1020

Val Gln  Ala Arg Leu Trp Phe  Leu Ala Gln Leu Glu  Pro Glu Ser
    1025            1030             1035

Thr Ala  Tyr Asn Val Pro Val  Ala Leu Arg Leu His  Gly Pro Leu
    1040            1045             1050

Gln Val  Glu Ala Leu Leu Asp  Ala Val Arg Asp Leu  Ala Glu Arg
    1055            1060             1065

His His  Val Leu Arg Ser Val  Ile Asp Asp Ser Gly  Ala Glu Pro
    1070            1075             1080

Val Leu  Val Val Arg Pro Ala  Gly Glu Val Pro Val  Ser Thr Ala
    1085            1090             1095

Asp Ile  Asp Arg Ser Arg Val  Glu Asp Ala Val Ala  Ala Gln Leu
    1100            1105             1110

Ala Thr  Pro Phe Ala Leu Asp  Arg Glu Pro Pro Met  Arg Ala Val
    1115            1120             1125

Leu Phe  Ala Val Gly Asp Arg  Glu His Val Leu Ser  Leu Thr Phe
    1130            1135             1140

His His  Ile Ala Thr Asp Ala  Trp Thr Arg Gly Leu  Leu Leu Ser
    1145            1150             1155

Glu Leu  Ser Ala Leu Tyr Ala  Ala Arg Ile Gly Leu  Arg Pro Thr
    1160            1165             1170

Pro Glu  Pro Pro Pro Ala Gln  Tyr Ala Glu Val Ala  Pro Val Pro
    1175            1180             1185

Asp Leu  Ala Asp Leu Asp Trp  Trp Ala Glu Gln Leu  Arg Gly Leu
    1190            1195             1200

Pro Pro  Val Leu Asp Leu Pro  Thr Asp Arg Pro Arg  Pro Ala Val
    1205            1210             1215

Ala Asp  Pro Gly Gly Ala Ser  Val Asp Leu Glu Leu  Pro Ala Glu
    1220            1225             1230

Leu Ser  Glu Arg Val Arg Ala  Val Ala Thr Ala Tyr  Arg Ala Thr
    1235            1240             1245

Pro Phe  Ile Val Leu Leu Ala  Gly Leu Gln Ala Leu  Leu Ala Arg
    1250            1255             1260

Leu Ser  Ala Gly Thr Asp Ile  Ala Val Gly Val Pro  Val Ala Gly
    1265            1270             1275

Arg Asp  His Pro Asp Ser Glu  Gly Val Ile Gly Cys  Phe Leu Asn
    1280            1285             1290

Thr Val  Val Val Arg Thr Asp  Val Gly Gly Glu Pro  Thr Gly His
    1295            1300             1305

Glu Leu  Leu Ala Arg Val Arg  Glu Thr Ala Leu Gly  Ala Phe Ala
    1310            1315             1320

His Ala  Ser Ala Pro Phe Asp  Arg Val Val Asp Arg  Leu Arg Pro
    1325            1330             1335
```

```
Glu Arg Asn Leu Ala Ala Thr Pro Leu Phe Gln Val Met Leu Asn
    1340                1345                1350

Tyr Phe Pro Asp Thr Gly Arg Pro Glu Leu Pro Gly Leu Glu Ala
    1355                1360                1365

Ala Glu Ile His Leu Pro Glu Gln Thr Ala Lys Phe Asp Leu Asn
    1370                1375                1380

Trp His Val Ile Asp Ser Gly Pro Gly Arg Pro Leu Arg Gly Gly
    1385                1390                1395

Leu Gly Tyr Arg Thr Asp Leu Phe Asp Gly Ala Thr Ala Ala Arg
    1400                1405                1410

Phe Thr Arg Trp Tyr Leu Ala Leu Leu Asp Gly Met Leu Ser Asp
    1415                1420                1425

Leu Glu Ala Pro Val Gly Ala Gln Pro Leu Glu Pro Val Thr Gly
    1430                1435                1440

Pro Ile Leu Ala Gly Glu Pro Leu Pro Ala Val Ala Asp Thr Pro
    1445                1450                1455

Val His Arg Leu Ile Glu Arg Trp Val Asp Thr Thr Pro Asp Ala
    1460                1465                1470

Pro Ala Val Val Gly Ala Asp Arg Gly Leu Thr Tyr Ala Glu Leu
    1475                1480                1485

Glu Thr Ala Ala Asn Arg Ile Ala His Trp Leu Leu Ala Ala Gly
    1490                1495                1500

Val Gly Ala Asp Glu Pro Val Gly Val Leu Leu Glu Pro Gly Ala
    1505                1510                1515

Asp Leu Ala Cys Ala Leu Phe Gly Ile Gln Lys Ser Gly Gly Gly
    1520                1525                1530

Tyr Leu Pro Met Asp Pro Ala Tyr Pro Ala Ala Arg Ile Ala Thr
    1535                1540                1545

Met Leu Asp Ala Ala Gly Val Arg Ala Val Val Thr Thr Ala Glu
    1550                1555                1560

Phe Ala Gly Leu Ile Gly Pro Asp Arg Trp Val Leu Ala Leu Asp
    1565                1570                1575

Arg Leu Pro Ser Leu Pro Arg Thr Arg Pro Glu Val Asp Val Arg
    1580                1585                1590

Pro Glu His Leu His His Val Ile Phe Thr Ser Gly Ser Thr Gly
    1595                1600                1605

Thr Pro Lys Ala Val Ala Ala Glu His Arg Gly Val Met Ser Tyr
    1610                1615                1620

Leu Asn Gly Met Leu Pro Arg Ile Gly Val Pro Gly Gly Ser Tyr
    1625                1630                1635

Ala Val Val Ser Thr Pro Ala Ala Asp Phe Gly Leu Thr Cys Val
    1640                1645                1650

Phe Gly Ala Leu Thr Thr Gly Gly Thr Val His Leu Val Pro Arg
    1655                1660                1665

Glu Thr Ala Met Asp Pro Ala Ala Phe Ala Gly Tyr Leu Ser Ala
    1670                1675                1680

His His Val Asp Val Val Lys Cys Val Pro Ser His Leu Glu Leu
    1685                1690                1695

Leu Ala Ser Gly Gly Asp Leu Ala Ala Val Leu Pro Asp Arg Leu
    1700                1705                1710

Leu Ile Leu Ala Gly Glu Ala Cys Pro Trp Asp Leu Val Glu Arg
    1715                1720                1725
```

```
Ala Arg Ala Ala Arg Pro Gly Leu Arg Ile Gln Ser His Tyr Gly
    1730                1735                1740

His Thr Glu Ser Thr Met Ile Cys Leu Val Cys Asp Thr Glu Glu
    1745                1750                1755

Ile Ala Ala Glu His Arg Thr Gly Ile Val Pro Leu Gly Arg Pro
    1760                1765                1770

Leu Pro Gly Val Tyr Gly His Leu Val Asp Ala Ser Arg Arg Pro
    1775                1780                1785

Val Pro Ala Gly Val Pro Gly Glu Leu Val Val Gly Gly Pro Gly
    1790                1795                1800

Val Thr Arg Gly Tyr Ile Gly Leu Pro Glu Leu Thr Ala Glu Arg
    1805                1810                1815

Phe Val Pro Asp Pro Leu Thr Gly Gln Gly Arg Cys Tyr Arg Ser
    1820                1825                1830

Gly Asp Leu Leu Arg Val Thr Ala Asp Gly Arg Val Glu Phe Arg
    1835                1840                1845

Gly Arg Val Asp Asp Gln Val Lys Val Arg Gly Tyr Arg Val Glu
    1850                1855                1860

Leu Gly Glu Val Thr Thr Ala Leu Arg Ala Leu Pro Gln Ile Ala
    1865                1870                1875

Asp Ala Val Val Leu Pro Val Gly Glu Gly Lys Ala Arg Gln Leu
    1880                1885                1890

Ala Ala Trp Val Thr Pro Ser Thr Val Asp Thr Ser Ala Ile Arg
    1895                1900                1905

Ser Ala Leu Arg Glu Arg Leu Pro Asp Tyr Met Val Pro Ala Gln
    1910                1915                1920

Phe Val Val Leu Asp Arg Ile Pro Leu Asn Pro Asn Gly Lys Val
    1925                1930                1935

Asp Arg Ala Ala Leu Pro Glu Pro Arg Pro Glu Thr Ala Glu Phe
    1940                1945                1950

Val Pro Pro Ser Thr Ala Gly Glu Glu Leu Val Ala Arg Ala Trp
    1955                1960                1965

Ala Gln Val Leu Gly Val Ala Arg Val Gly Ala His Asp Asp Phe
    1970                1975                1980

Phe Ala Leu Gly Gly Asp Ser Phe Ala Ala Val Arg Ala Val Lys
    1985                1990                1995

Glu Ile Gly Cys Gly Leu Arg Val Ile Asp Leu Phe Thr Arg Pro
    2000                2005                2010

Thr Val Ala Glu Leu Ala Ala Phe Leu Asp Arg Arg Asp Gly Gly
    2015                2020                2025

Gly Leu Leu His Arg Leu Gly Gly Gly Arg Thr Ser Glu Phe Thr
    2030                2035                2040

Leu Val Cys Leu Pro Tyr Gly Gly Gly Ser Ala Ala Val Tyr Gln
    2045                2050                2055

Pro Leu Ala Trp Ala Leu Gly Glu Arg Val Glu Val Leu Ser Ala
    2060                2065                2070

Glu Leu Pro Gly His Asp Pro Ala Arg Pro Asp Glu Leu Pro Leu
    2075                2080                2085

Pro Leu Glu Glu Leu Val Glu Ala Leu Ser Ala Glu Val Ala Thr
    2090                2095                2100

Thr Ala Ser Gly Pro Ile Ala Ile Tyr Gly His Cys Val Gly Ser
    2105                2110                2115

Ala Pro Ala Val Ala Leu Ala Arg Arg Leu Glu Ala Asp Gly Ile
```

-continued

```
                2120                2125                2130
Pro Val Leu Gly Val Ile Ala Ala Gly Ser Phe Pro Thr Ala Gln
    2135                2140                2145
Leu Pro Gly Leu Ala Arg Arg Ile Phe Arg Ser Asp Arg Trp Val
    2150                2155                2160
Ser Asp Arg Met Phe Gln Asp Ala Leu Arg Ala Thr Gly Gly Leu
    2165                2170                2175
Leu Asp Asp Met Asp Glu Ala Ala Lys Gln Val Ala Val Arg Ala
    2180                2185                2190
Met Arg His Asp Ala Asp Gln Ala Gln Glu Trp Phe Ser Arg Glu
    2195                2200                2205
Leu Thr Gly Gly Gly Pro Pro Leu Arg Ala Pro Ile Leu Cys Val
    2210                2215                2220
Val Gly Glu Arg Asp Arg Ala Thr Glu Leu His Gln Glu Arg Tyr
    2225                2230                2235
Ala Glu Trp Thr Ala Phe Ala Pro Arg Val Glu Leu Ala Val Leu
    2240                2245                2250
Pro His Ala Gly His Tyr Phe Leu Arg His Gln Ala Glu Pro Leu
    2255                2260                2265
Ala Ala Leu Val Ile Glu His Leu Arg Ser Trp Ala Ala Gly Arg
    2270                2275                2280
Leu Pro Asp Pro Val Arg Pro Pro Asp Arg Thr Gly Leu Arg Pro
    2285                2290                2295
Phe Tyr Thr Val Ala Gly Gly Gln Phe Val Ser Val Val Gly Thr
    2300                2305                2310
Ala Leu Ser Ser Phe Ala Leu Gly Val Trp Ala Tyr Gln Asp Ser
    2315                2320                2325
Gly Arg Ile Leu Asp Leu Ala Leu Ile Val Met Leu Ser Gln Ile
    2330                2335                2340
Pro Ala Val Leu Leu Thr Pro Leu Gly Gly Ala Leu Ala Asp Arg
    2345                2350                2355
Val Asp Arg Arg Arg Ile Met Leu Val Ser Asp Ala Val Ser Gly
    2360                2365                2370
Leu Ala Met Ala Ala Leu Val Leu Leu Leu Val Thr Asp Arg Leu
    2375                2380                2385
Ala Leu Trp Asn Val Cys Leu Ile Val Gly Val Thr Ser Leu Ala
    2390                2395                2400
Thr Ala Phe Gln Gln Pro Ala Tyr Leu Ala Ala Ile Ala Gln Leu
    2405                2410                2415
Val Pro Lys Pro Tyr Leu Pro Gln Ala Asn Ala Val Ala Asn Leu
    2420                2425                2430
Gly Phe Gly Ile Gly Asn Val Val Ala Pro Leu Ala Gly Gly Ala
    2435                2440                2445
Leu Ile Gly Met Phe Gly Leu Ser Ala Val Val Ala Ile Asp Val
    2450                2455                2460
Ala Ser Phe Gly Val Gly Val Ala Thr Leu Leu Ala Val Arg Phe
    2465                2470                2475
Pro Asp Arg Leu Phe His Arg Gln Glu Glu Thr Phe Arg Ala Ala
    2480                2485                2490
Leu Thr Gly Gly Trp Leu Phe Leu Arg Arg Arg Pro Leu Leu
    2495                2500                2505
Val Met Ala Val Tyr Phe Ala Val Val Asn Phe Cys Thr Ala Leu
    2510                2515                2520
```

```
Met Trp Val Leu Ile Thr Pro Val Val Ala Leu Gly Ser Ser
    2525                2530                2535

Ala Ala Leu Gly Ala Val Thr Ala Val Gly Gly Leu Gly Ala Ala
        2540                2545                2550

Val Gly Thr Ala Val Val Leu Val Trp Gly Gly Thr Arg Arg Arg
        2555                2560                2565

Ala Thr Gly Met Val Gly Phe Val Ile Gly Ser Gly Ile Gly Val
        2570                2575                2580

Val Leu Met Gly Val Trp Pro Ala Leu Trp Leu Val Ala Ala Gly
        2585                2590                2595

Leu Phe Leu Arg Leu Ala Cys Met Ser Ile Gly Asn Ala His Trp
        2600                2605                2610

Leu Ser Ile Ile Gln Val Lys Val Gly Pro Glu Leu Gln Gly Arg
        2615                2620                2625

Val Leu Ala Val Asn Val Met Leu Ala Thr Ala Met Gln Pro Leu
        2630                2635                2640

Gly Phe Leu Ala Ala Gly Pro Leu Ala Asp Trp Ala Gln Ser Tyr
        2645                2650                2655

Thr Ser Gly Pro Gly Arg Gly Ala Ala Ala Val Leu Leu Val Ser
        2660                2665                2670

Gly Val Phe Leu Val Val Trp Gly Val Ile Gly Leu Arg Tyr Arg
        2675                2680                2685

Pro Leu His His Leu Glu Asp Leu Val Pro Asp Ala Ala Pro Pro
        2690                2695                2700

Pro Glu Ala Glu Ala Asp Leu Asp Ala Ile Gln Ala Lys Val Leu
        2705                2710                2715

Ser Gly
    2720

<210> SEQ ID NO 4
<211> LENGTH: 1769
<212> TYPE: PRT
<213> ORGANISM: Catenulispora acidiphila

<400> SEQUENCE: 4

Met Pro Pro Leu Ser Phe Ala Gln Glu Arg Leu Trp Phe Met Glu Gln
1               5                   10                  15

Leu Ala Pro Gly Ser Ala Ala His Thr Val Pro Val Ala Leu Arg Leu
                20                  25                  30

Arg Gly Ala Leu Asp Pro Asp Ala Phe Gly Arg Ala Leu Arg Asp Leu
            35                  40                  45

Ala Gly Arg His Glu Thr Leu Arg Met Ser Tyr Pro Ala Asp Thr Asp
        50                  55                  60

Asp Arg Pro Gly Ile His Val Ala Ala Gly Glu Val Pro Leu Arg
65                  70                  75                  80

Ile Ser Asp Ala Asp Ser Leu Asp Ala Ala Gln Asp Val Val Gly Ala
                85                  90                  95

Met Ile Ala Glu Pro Phe Asp Ile Val Arg Gly Pro Val Ala Arg Ala
                100                 105                 110

Leu Leu Val Arg Leu Ala Asp Asp His Val Leu Ala Leu Ala Val
            115                 120                 125

His His Ile Ala Cys Asp Gly Trp Ser Val Asp Val Leu Leu Thr Asp
        130                 135                 140

Leu Phe Ala Leu Tyr Glu Ala Arg Leu Ala Gly Ala Pro Ser Thr Leu
```

```
            145                 150                 155                 160
        Pro Glu Pro Ala Ile Gly Tyr Gly Asp Tyr Ala Ile Trp Gln Arg Asp
                        165                 170                 175
        Arg Pro Gly Tyr Asp Thr Asp His Ala Tyr Trp Ala Ala Gln Leu Ala
                        180                 185                 190
        Gly Leu Pro Thr Leu Asp Leu Val Thr Asp Arg Ile Arg Pro Pro Glu
                        195                 200                 205
        Gln Thr Tyr Asn Gly Ala Ala His Gly Phe Arg Leu Asn Arg Thr Leu
                        210                 215                 220
        Thr Asp Ser Val Lys Ala Leu Ala Asp Arg Ser Gln Ala Thr Pro Tyr
        225                 230                 235                 240
        Met Val Leu Leu Ala Ala Phe Gln Ala Leu Leu Ala Arg Tyr Thr Ser
                        245                 250                 255
        Gln Asp Asp Phe Ala Val Gly Ser Pro Val Ala Gly Arg Thr Leu Pro
                        260                 265                 270
        Glu Leu Glu Pro Leu Val Gly Cys Phe Val Asn Met Leu Thr Met Arg
                        275                 280                 285
        Ala Asp Leu Thr Gly Arg Pro Ser Phe Thr Asp Leu Leu Ala Arg Val
                        290                 295                 300
        Gln Glu Thr Ala Ser Ala Ala Tyr Asp His Gln Leu Pro Phe Glu
        305                 310                 315                 320
        Gln Leu Val Gln Arg Leu Asp Leu Pro Arg Asp Val Ala Arg Ala Pro
                        325                 330                 335
        Leu Phe Gln Val Ile Phe Ala Met Gln Asn Tyr Gln Arg Gly Ser Ala
                        340                 345                 350
        Ala Gly Ala Ser Gly Thr Leu Ser Ala Glu Pro Phe Pro Leu Thr Ser
                        355                 360                 365
        Trp Ala Thr Arg Tyr Asp Leu Glu Leu Tyr Ile Ser Gln Asp Gly Asp
                        370                 375                 380
        Ala Leu Asp Ala Leu Phe Val Tyr Asn Thr Asp Leu Phe Gly Ala Glu
        385                 390                 395                 400
        Thr Ile Ala Arg Leu Ala Asn His Phe Thr Ala Leu Leu Thr Ala Ala
                        405                 410                 415
        Leu Asp Ala Pro Glu Leu Pro Val Ala Asp Ala Glu Met Leu Asp Ala
                        420                 425                 430
        Ala Glu Arg Ala Arg Leu Leu Ala Asp Phe Asn Ala Thr Thr Ser Asp
                        435                 440                 445
        Phe Pro Gln Asp Lys Thr Leu His Glu Leu Val Glu Ala Gln Cys Ala
                        450                 455                 460
        Arg Thr Pro Asp Ala Val Ala Ile Glu Phe Glu Gly Glu Ser Leu Thr
        465                 470                 475                 480
        Tyr Arg Glu Val Asn Thr Gln Ala Asp Ala Val Ala Tyr Arg Leu Ser
                        485                 490                 495
        Glu Leu Gly Val Gly Pro Glu Ser Leu Val Ala Val Cys Ala Glu Arg
                        500                 505                 510
        Ser Leu Ala Leu Pro Val Ala Leu Leu Gly Val Leu Lys Ser Gly Ala
                        515                 520                 525
        Ala Tyr Leu Pro Leu Asp Pro Glu Tyr Pro Pro Asp Arg Leu Ala Phe
                        530                 535                 540
        Met Leu Ala Asp Ala Gly Val Pro Val Ile Leu Ala Gln Arg Gly Leu
        545                 550                 555                 560
        Leu Asp Gln Leu Pro Glu Thr Ser Ala Thr Ile Gln Tyr Leu Asp Glu
                        565                 570                 575
```

```
Ala Thr Asn Leu Ala Ala Pro Pro Gly Trp Arg Ala Pro Arg Gly Asp
            580                 585                 590

Leu Ala Tyr Ala Ile Tyr Thr Ser Gly Ser Thr Gly Arg Pro Lys Gly
        595                 600                 605

Val Leu Asn Thr His Arg Ala Ile Val Asn Arg Leu Asp Trp Met Gln
    610                 615                 620

Arg Arg Tyr Gln Leu Thr Ala Asp Asp Val Val Leu Gln Lys Thr Pro
625                 630                 635                 640

Ala Gly Phe Asp Val Ser Val Trp Glu Phe Phe Trp Pro Leu Leu Ala
            645                 650                 655

Gly Ala Arg Leu Val Leu Ala Arg Pro Gly Gly His Lys Asp Ala Gly
        660                 665                 670

Tyr Leu Arg Asp Leu Ile Arg Ser Ala Gly Val Thr Thr Ala His Phe
    675                 680                 685

Val Pro Ser Met Leu Gly Val Phe Leu Ala Glu Glu Gly Val Glu Gln
    690                 695                 700

Cys Arg Gly Leu Arg Arg Ile Leu Cys Ser Gly Glu Glu Leu Pro Val
705                 710                 715                 720

Asp Val Ala Leu Arg Cys Leu Ala Thr Leu Pro Ala Glu Leu His Asn
            725                 730                 735

Leu Tyr Gly Pro Thr Glu Ala Ala Ile Asp Val Ser Ser Trp Gln Cys
        740                 745                 750

Thr Pro Gln Glu Leu Thr Ala Ala Arg Val Pro Ile Gly Leu Pro
    755                 760                 765

Ile Gln Asn Leu Ala Leu His Val Leu Asp Pro Gln Met Gln Pro Val
    770                 775                 780

Pro Ile Gly Val Pro Gly Glu Leu Phe Leu Gly Gly Val Gly Leu Ala
785                 790                 795                 800

Arg Gly Tyr Leu Lys Arg Pro Ala Leu Thr Ala Glu Arg Phe Val Pro
            805                 810                 815

Asp Pro Phe Gly Thr Pro Gly Ser Arg Leu Tyr Arg Thr Gly Asp Leu
        820                 825                 830

Ala Arg Arg Arg Thr Asp Gly Ala Val Glu Phe Leu Gly Arg Ile Asp
    835                 840                 845

Gly Gln Val Lys Ile Arg Gly Leu Arg Ile Glu Leu Gly Glu Ile Glu
850                 855                 860

Ala Ala Leu Arg Asp Gln Pro Gly Val Ala Asp Ala Ala Val Val
865                 870                 875                 880

Arg Glu Asp Val Pro Gly Asp Arg Arg Ile Val Gly Tyr Val Val Gly
            885                 890                 895

Glu Ala Asp His Ala Ala Leu Arg Thr Ala Leu Lys Gln Arg Leu Pro
        900                 905                 910

Asp Tyr Met Val Pro Ser Ala Leu Val Thr Leu Asp Val Leu Pro Leu
    915                 920                 925

Thr Pro Asn Gly Lys Leu Asp Arg Arg Ala Leu Pro Glu Pro Gln Arg
    930                 935                 940

Gly Arg Asp Glu Gly Thr Ala Phe Ala Ala Pro Glu Ser Asp Ser Gln
945                 950                 955                 960

Arg Leu Ile Ala Gln Ile Trp Ser Asp Val Leu Arg Val Glu Arg Ile
            965                 970                 975

Gly Ile Asp Asp Asp Phe Phe Asp Leu Gly Gly His Ser Leu Leu Ala
        980                 985                 990
```

```
Ala Gln Val Val Ala Lys Leu Arg  Arg Ser Ala Gly Ala  Gly Val Ser
         995               1000                1005

Val Leu Asp Leu Phe Lys Asn  Pro Thr Val Arg Gly  Leu Ala Thr
    1010              1015                 1020

Leu Leu Asp Thr Pro Ala Ala  Glu Arg Gly Pro Ala  Glu Leu Val
    1025              1030                 1035

His Glu Leu Thr Lys Pro Ile  Pro Val Ala Gln Arg  Thr Leu Ser
    1040              1045                 1050

Phe Val Cys Val Pro Tyr Gly  Gly Gly Ser Ala Ile  Val Tyr Gln
    1055              1060                 1065

Pro Leu Ala Asp Ala Leu Pro  Asp Gly His Arg Leu  Phe Ala Val
    1070              1075                 1080

Ala Ile Pro Gly His Asp Ile  Gly Leu Asp Glu Asp  Ala Leu Pro
    1085              1090                 1095

Phe Asp Glu Leu Ala Ser Arg  Cys Val Glu Glu Ile  Leu Arg Lys
    1100              1105                 1110

Val Asp Gly Pro Leu Ala Val  Tyr Gly His Cys Gly  Val Gly Ser
    1115              1120                 1125

Ala Leu Ala Val Glu Ile Ala  Arg Arg Leu Glu Ala  Ala Gly Arg
    1130              1135                 1140

Arg Leu Glu Ala Leu Tyr Ile  Gly Ala Ile Phe Pro  Phe Ala Arg
    1145              1150                 1155

Pro Glu Asn Lys Val Leu Gly  Gly Leu Ser Arg Val  Ala Arg Leu
    1160              1165                 1170

Glu Arg Phe Arg Ser Asp Arg  Gly Tyr Ala Asn Trp  Leu Leu Ser
    1175              1180                 1185

Met Gly Val Asp Met Ser Asp  Ile Glu Pro Glu Gln  Ala Thr His
    1190              1195                 1200

Ile Ile Gln Asn Met Arg Lys  Asp Ser Gln Ser Ala  Glu Asp Tyr
    1205              1210                 1215

Tyr Thr Gly Leu Leu Arg Asp  Ser Val Asp Arg Leu  Arg Ala Pro
    1220              1225                 1230

Val Ile Thr Val Ala Gly Asp  Arg Asp Pro Thr Thr  Asp Phe Tyr
    1235              1240                 1245

Ala Glu Arg Tyr Arg Glu Trp  His Phe Leu Thr Asp  Thr Ser Ala
    1250              1255                 1260

Val Val Val Leu Asp Glu Ala  Gly His Phe Phe Leu  Lys Tyr Arg
    1265              1270                 1275

Ala Glu Glu Leu Ala Ala Ile  Val Thr Glu Thr Arg  Pro Ala Leu
    1280              1285                 1290

Glu Thr Pro Glu Pro Leu Ser  Arg Gln Glu Arg Gly  Ala Asp Ala
    1295              1300                 1305

Gly Trp Trp Leu His Gly Val  Ser Arg Ser Arg Glu  Arg Val Val
    1310              1315                 1320

Pro Thr Gly Pro Thr Pro Ser  Met Arg Arg Phe Leu  Ala Val Ala
    1325              1330                 1335

Ser Gly Gln Leu Val Ser Met  Thr Gly Ser Ala Leu  Thr Glu Phe
    1340              1345                 1350

Ala Val Pro Leu Trp Ile Tyr  Leu His Thr Gly Ser  Leu Phe Arg
    1355              1360                 1365

Phe Ala Leu Phe Ala Val Cys  Gly Leu Val Pro Gly  Met Leu Ala
    1370              1375                 1380

Ala Pro Leu Ala Gly Ala Val  Val Asp Arg Ser Asn  Arg Arg Arg
```

```
                        1385                1390                1395
Val Met Leu Leu Gly Asp Thr Phe Ala Gly Thr Gln Leu Ile
    1400                1405                1410

Leu Gly Ile Leu Leu Trp Thr Gly His Leu Gln Ile Trp His Ile
    1415                1420                1425

Tyr Pro Leu Leu Ile Cys Leu Ser Val Ser Leu Thr Phe Gln Arg
    1430                1435                1440

Leu Ala Tyr Gly Ser Ser Val Ala Gln Leu Val Pro Lys His Tyr
    1445                1450                1455

Leu Gly His Ala Asn Gly Val Val Gln Met Ile Asn Gly Val Ala
    1460                1465                1470

Gln Ile Met Val Pro Leu Val Ala Val Gly Leu Met Ala Ala Ile
    1475                1480                1485

Gly Leu Gly Gly Ile Leu Val Ile Asp Val Ala Ser Tyr Ala Val
    1490                1495                1500

Ala Val Ala Val Val Leu Ala Val Arg Phe Pro Ala Thr Met Ala
    1505                1510                1515

Trp Arg Arg Lys Glu Thr Leu Leu Ala Glu Ile Ala Glu Gly Phe
    1520                1525                1530

Arg Tyr Ser Trp Gly Gln Pro Gly Leu Arg Ala Met Leu Leu Phe
    1535                1540                1545

Phe Ala Ala Leu Asn Val Phe Leu Ser Pro Leu Phe Leu Leu Ile
    1550                1555                1560

Ser Pro Leu Val Leu Ser Phe Thr Thr Leu Ser Arg Val Gly Glu
    1565                1570                1575

Val Ala Leu Ala Ala Gly Ile Gly Ala Thr Leu Gly Gly Leu Thr
    1580                1585                1590

Met Thr Phe Trp Gly Gly Pro Arg Arg Leu Arg Met Arg Gly Met
    1595                1600                1605

Leu Leu Cys Thr Leu Ala Leu Ala Ala Phe Cys Leu Val Thr Gly
    1610                1615                1620

Leu Arg Pro Thr Leu Trp Leu Ile Ala Val Gly Ala Phe Gly Met
    1625                1630                1635

Ser Tyr Trp Leu Thr Val Val Asn Gly Ile Tyr Thr Thr Ile Val
    1640                1645                1650

Gln Val Lys Val Ala Gln Arg Phe His Gly Arg Val Phe Ala Leu
    1655                1660                1665

Asn Thr Leu Ile Ala Trp Ser Thr Leu Pro Ile Gly Trp Gly Leu
    1670                1675                1680

Ile Val Pro Tyr Gly Thr Lys Leu Phe Gln Pro His Ile Gly Arg
    1685                1690                1695

Met Tyr Pro Val Leu Ala Ala Gly Met Val Leu Val Val Leu Ala
    1700                1705                1710

Ala Leu Arg Thr Pro Ala Leu Arg Arg Phe Asp Ile Asp Val Pro
    1715                1720                1725

Asp Ser Val Pro Asp Asp Leu Ile Gly Leu Glu Ala Arg Gln Arg
    1730                1735                1740

Arg Pro Arg Thr Ala Glu Pro Ala Ile Pro Ala Glu Leu Thr Glu
    1745                1750                1755

Pro Val Ala Glu Pro Ala Ala Gly Ser Val Arg
    1760                1765

<210> SEQ ID NO 5
```

<211> LENGTH: 562
<212> TYPE: PRT
<213> ORGANISM: Pyrobaculum aerophilum

<400> SEQUENCE: 5

```
Met Ser Val Gln Val Ser Phe Arg Gln Val Ala Ser Val Ala Ala Val
1               5                   10                  15

Ala Trp Ser Gly Ala Phe Leu Glu Trp Val Asp Phe Tyr Thr Tyr Ala
            20                  25                  30

Leu Leu Ala Val Ile Val Ala Lys Val Phe Phe Pro Ser Ala Asp Pro
        35                  40                  45

Ile Ala Ser Leu Leu Ala Ser Phe Ala Ala Leu Ala Ile Gly Phe Leu
    50                  55                  60

Phe Arg Pro Leu Gly Ala Ile Leu Phe Gly Lys Leu Gly Asp Gln Phe
65                  70                  75                  80

Gly Arg Lys Ile Ala Phe Ile Ala Ala Met Ile Leu Met Leu Ala Gly
                85                  90                  95

Thr Leu Gly Ile Gly Leu Leu Pro Gly Tyr Ala Glu Ile Gly Ile Leu
            100                 105                 110

Ala Ser Ile Gly Val Phe Ile Leu Arg Ile Ile Gln Gly Leu Ala Leu
        115                 120                 125

Gly Gly Gly Tyr Gly Ala Ala Ile Thr Tyr Leu Gly Glu Phe Val Pro
    130                 135                 140

Glu His Arg Arg Gly Phe Phe Thr Gly Phe Leu Phe Thr Thr Pro Pro
145                 150                 155                 160

Ala Gly Met Ala Thr Val Gly Ala Leu Ile Trp Leu Phe Ser Asn Ile
                165                 170                 175

Leu Gly Thr Gln Ala Phe Asn Ala Trp Gly Trp Arg Leu Asn Phe Ile
            180                 185                 190

Val Ala Gly Val Ile Val Phe Ile Ile Val Leu Ile Met His Met Phe
        195                 200                 205

Tyr Lys Glu Thr Pro Val Phe Ser Met Leu Lys Ala Val Arg Arg Val
    210                 215                 220

Thr Ser Ala Pro Ile Arg Glu Val Phe Ser Arg Arg Tyr Leu Pro Leu
225                 230                 235                 240

Val Leu Met Ala Trp Ile Gly Val Val Gly Ala His Gly Pro Ile Trp
                245                 250                 255

Tyr Thr Asn Gln Leu Phe Asn Ala Tyr Tyr Ile Gly Pro Asn Phe Gln
            260                 265                 270

Asn Tyr Val Asp Ala Ala Thr Ala Ser Ala Leu Leu Ser Thr Ala Thr
        275                 280                 285

Tyr Ala Ala Leu Trp Met Tyr Pro Leu Phe Gly Tyr Ile Ser Asp Arg
    290                 295                 300

Ile Gly Arg Lys Pro Val Leu Leu Gly Ile Tyr Gly Asn Ala Leu
305                 310                 315                 320

Trp Phe Pro Ile Ala Phe Trp Leu Ile Asp Gln Val Gly Pro His Lys
                325                 330                 335

Asp Leu Thr Ala Leu Trp Leu Phe Trp Ser Met Thr Leu Phe Asn
            340                 345                 350

Gly Ile Gly Tyr Ser Gly Ala Met Ser Ala Phe Leu Leu Glu Leu Phe
        355                 360                 365

Pro Ala Arg Ile Arg Leu Ser Ala Val Ala Leu Ala Tyr Asn Leu Gly
    370                 375                 380

Tyr Gly Val Thr Gly Gly Leu Thr Pro Phe Val Ile Thr Trp Ile Tyr
```

```
385                 390                 395                 400
Ser Ile Thr His Asn Ile Tyr Leu Ser Thr Leu Leu Trp Ser Thr Val
                405                 410                 415

Val Pro Met Ile Met Ala Thr Trp Tyr Val Leu Lys Gly Pro Glu Thr
                420                 425                 430

Leu Gly Val Arg Ile Trp Ala Glu Phe Ala Thr Glu Lys Phe Ala Lys
                435                 440                 445

Lys Thr Val Thr Leu Pro Ala Thr Thr Pro Ile Arg Gln Val Ile Ser
                450                 455                 460

Ala Leu Val Ser Ala Gly Ser Lys Tyr Ala Val Leu Thr Gly Ser Val
465                 470                 475                 480

Val Gly Ile Phe Gly Thr Arg Ser Leu Leu Arg Ala Leu Ser Ala Gly
                485                 490                 495

Ala Lys Leu Glu Glu Pro Ala Gly Asn Tyr Ala Thr Lys Val Pro Cys
                500                 505                 510

Ile Asn Ala Asp His Pro Val Thr Glu Val Phe Val Ala Leu Glu Gln
                515                 520                 525

Tyr Asn Val Arg Ala Val Pro Val Cys Lys Gly Asn Glu Val Ile Gly
                530                 535                 540

Ile Val Glu Ala Ser Arg Phe Asn Lys Arg Ile Ala Cys Ala Lys Lys
545                 550                 555                 560

Arg Ile

<210> SEQ ID NO 6
<211> LENGTH: 1429
<212> TYPE: PRT
<213> ORGANISM: Emericella nidulans

<400> SEQUENCE: 6

Met Thr Pro Lys Thr Asp Ala Lys Ala Leu Pro Ile Val Lys Asn Gln
1               5                   10                  15

Leu Arg Glu Ile Trp Ala Glu Val Leu Gln Asp Gly Pro Glu Asn Phe
                20                  25                  30

Leu Asp Glu Asp Val Phe Phe Asp Val Gly Gly Asp Ser Val Arg Ser
                35                  40                  45

Gln Lys Leu Ile Ile Ala Ala Glu Lys Arg Gly Ile Arg Leu Thr Met
            50                  55                  60

Glu Gln Asn Phe Leu Asn Ala Ser Leu Glu Glu Met Ala Gly Val Ala
65              70                  75                  80

Lys Val Val Pro Val Lys Leu Gln Lys Gln Asp Ala Asp Asp Ala Pro
                85                  90                  95

Lys Ala Phe Ala Leu Leu Gln Asp Leu Gly Tyr Gly Thr Leu Gln Asp
                100                 105                 110

Ile Leu Asp Thr Val Ser Ser Gln Cys Arg Leu Ser Thr Asp Gln Ile
            115                 120                 125

Ala Asp Val Tyr Ser Cys Ser Pro Met Gln Glu Ser Leu Val Ala Gln
            130                 135                 140

Leu Asp Gly Val Ala Asn Leu Tyr Val Arg Gln Leu Val Phe Arg Phe
145             150                 155                 160

Ala Gln Ser Thr Pro Leu Asp Val Phe Lys Gln Ala Trp Glu Arg Thr
                165                 170                 175

Val Gln Ala Asn Pro Val Leu Arg Thr Arg Ile Cys Val Ala Pro Gly
                180                 185                 190

Glu Arg Gly Tyr Leu Gln Ala Val Val Glu Glu Ala Pro Ser Trp Ser
```

```
                195                 200                 205
Ala Ser Glu Ile Ser Leu Ser Arg Phe Leu Glu Lys Asp Ala Val Asp
210                 215                 220
Ala Met Asn Pro Gly Val Pro Phe Phe Arg Tyr Ala Leu Val Ala Asp
225                 230                 235                 240
Glu Ser His Gln Tyr Phe Val Trp Thr Ala His Ala Leu Cys Asp
                245                 250                 255
Gly Ala Ser Ile Pro Glu Ile Leu Ala Glu Val Ala Met Arg Cys Gln
                260                 265                 270
Gly Gln Cys Asp Ala Ile Leu Pro Arg Asp Pro Phe Arg Gly Phe Ile
                275                 280                 285
Glu Ser Met Phe Met Pro Asp Pro Glu Arg Gln Gln Gln Gln Arg Leu
                290                 295                 300
Phe Trp Arg His Ser Leu Glu Asp Leu Asn Leu Thr Pro Phe Pro Pro
305                 310                 315                 320
Pro Pro Arg Ser Asn Thr Leu Val Asn Pro Ala Ala Thr Val Glu Arg
                325                 330                 335
Leu Leu His Phe Gly Gln Gln Gln Met Pro Leu Gly Leu Thr Arg Ala
                340                 345                 350
Leu Leu Leu Arg Ala Ala Trp Ala Ile Leu Leu Ser His Tyr Thr Gly
                355                 360                 365
Thr Gln Asp Ile Ile Phe Gly Ala Ile Asn Ser Gly Arg Thr Thr Asp
                370                 375                 380
Val Pro Gly Ala Ser Arg Met Thr Gly Pro Thr Ile Asn Leu Val Pro
385                 390                 395                 400
Ile Val Leu Arg Val Glu Ala Gln Gln Pro Val Gly Gly Ser Ser Leu
                405                 410                 415
Thr Asp Phe Glu Ser Leu Leu Val Val Gln Ser Met Glu Phe Ala Asp
                420                 425                 430
Ala Ile Gly Pro Ala Thr Gln Tyr Leu Gly Leu Glu Tyr Val Asp Ala
                435                 440                 445
Leu Gly Lys Lys Glu His His Pro Tyr Pro Leu Ile Ala Thr Cys Thr
                450                 455                 460
Ile Leu Thr Asp Ser Thr Val Arg Leu Thr Leu Gln Tyr Asp Glu Gln
465                 470                 475                 480
Leu Leu Ser Ala Arg Gln Ala Gly Asn Leu Ser His Gln Phe Glu Ala
                485                 490                 495
Val Val Lys Gln Leu Thr Asp Ala Ala Ser Gln Ala Leu Leu Asp Ser
                500                 505                 510
Ile Ser Pro Leu Ser Glu His Asp Leu Ala Gln Ile His Glu Trp Asn
                515                 520                 525
Lys Leu Thr Pro Ser Pro Glu Glu Thr Cys Leu His His Leu Phe Ala
                530                 535                 540
Trp Gln Val Ser Val Gln Pro Asn Ala Pro Ala Gly Cys Leu Val Arg
545                 550                 555                 560
Gly Asp Ile Pro Ile Cys Phe Gly Asn Leu Leu Val Leu Pro Leu Phe
                565                 570                 575
Arg Thr Leu Gly Ala Arg Gly Asp Phe His Trp His Phe Thr Gln Ser
                580                 585                 590
Pro Val Asn Gly Gly Arg Lys Glu Gln Thr Leu Asn Glu Pro His Ile
                595                 600                 605
```

-continued

```
Val Glu Ser Asn Phe Leu Gln Arg Lys Met Ser Ser Leu Leu Ala Thr
610                 615                 620

Thr Thr Pro Ala Lys Glu Val Gly Phe Ser Phe Lys Gln Gly Val Asn
625                 630                 635                 640

Trp Ser Asp Tyr Leu Asp Tyr Arg Pro Val Tyr Pro Pro Phe Phe
            645                 650                 655

Glu Leu Ile Tyr Ser Tyr Arg Ala Gly Glu Leu Gly Ser Ser Trp Ser
            660                 665                 670

Glu Ala His Asp Ile Gly Ala Gly Cys Ser Ser Val Ser Ala Gly Leu
            675                 680                 685

Ala Ala Lys Phe Pro Ser Trp Asn His Thr Ala Val Ala Ile Arg Glu
690                 695                 700

Ile Gly Arg Glu Leu Lys Val Gly Gly Thr Leu Ala Val Thr His Tyr
705                 710                 715                 720

Thr Val Pro Arg Ile Val Gly Asn Arg Lys Ala Gln Asn Val Trp Lys
            725                 730                 735

Ala Ile Trp Glu Glu Tyr Ser Lys Arg Ala Thr Gly Pro Leu Leu Asp
            740                 745                 750

His Ala Val Ser Ile Val Asn Thr Ala Leu Asp Cys Leu Glu Ser Pro
            755                 760                 765

Gln His Glu Trp Gly Arg Val Asn Ala Gln Gly Ser Ile Glu Ser Tyr
            770                 775                 780

Gln Leu Asp Ser Arg Gly Lys Glu Ser Arg Val Lys Lys Ser Glu Glu
785                 790                 795                 800

Val Val Trp Val Glu Gly Asp Asp Trp Ala Asp Glu Gln Asp Val
            805                 810                 815

Thr Trp Phe Lys Gly Tyr Leu Ala Thr Trp Val Pro Val Pro Gly
            820                 825                 830

Asn Glu Ile Gln His Leu Trp Asn Asp Pro Glu Met Ala Leu Gly Gly
            835                 840                 845

Gly Lys Thr Arg Ala Leu Arg Ser Tyr Asn Ser Asn Tyr Thr Ile Gly
850                 855                 860

Ala Ile Asp Arg Pro Val Tyr Tyr Ala Met Ser Asp Tyr Thr Glu Asp
865                 870                 875                 880

Arg Ala Pro Asn Lys Ala Val Glu Ser Ser Asp Ser Leu Thr Asn Tyr
            885                 890                 895

Asn Pro Ile Pro Glu Asn Glu Lys Gln Gly Thr Val Pro Glu Pro Glu
            900                 905                 910

Ala Pro Pro Arg Asp Ile Asp Gly Trp Lys Trp Leu Ser Val Phe
            915                 920                 925

Cys Ile Trp Ser Ser Ile Phe Phe Tyr Ala Leu Asp Asn Thr Val Val
            930                 935                 940

Ala Asp Ile Gln Pro Val Ile Glu Ser Leu Gly Glu Leu Glu Lys
945                 950                 955                 960

Leu Thr Trp Leu Ser Val Ala Phe Leu Leu Gly Ala Thr Ala Thr Asn
            965                 970                 975

Leu Ile Trp Gly Lys Ile Tyr Gly His Phe Asn Val Lys Trp Thr Tyr
            980                 985                 990

Leu Phe Asn Val Ala Val Phe Glu  Ile Gly Ser Ala Ile  Cys Gly Ala
            995                 1000                1005
```

```
Ala Pro Ser Met Asn Val Met Ile Val Gly Arg Ala Leu Cys Gly
    1010                1015                1020

Val Ala Gly Ala Gly Leu Tyr Val Gly Val Met Thr Leu Leu Ala
    1025                1030                1035

Met Thr Thr Thr Leu Ser Glu Arg Pro Leu Tyr Val Gly Gly Thr
    1040                1045                1050

Gly Leu Thr Trp Gly Ile Gly Ile Val Leu Gly Pro Val Val Gly
    1055                1060                1065

Gly Gly Phe Ser Gln Ser Ser Val Gly Trp Arg Trp Ala Phe Tyr
    1070                1075                1080

Ile Asn Leu Leu Ile Gly Ala Val Cys Ala Pro Val Tyr Leu Phe
    1085                1090                1095

Leu Leu Pro Thr Lys Asp Pro Arg Pro Gly Val Ser Leu Lys Glu
    1100                1105                1110

Arg Ser Arg Glu Leu Asp Tyr Val Gly Ala Ile Leu Gln Met Gly
    1115                1120                1125

Ala Leu Thr Thr Phe Val Leu Ala Ile Ser Trp Gly Gly Val Thr
    1130                1135                1140

Tyr Pro Trp Asn Ser Gly Gln Val Ile Gly Cys Phe Val Ala Ser
    1145                1150                1155

Gly Val Leu Phe Ile Ile Leu Gly Leu Gln Gln Val Phe Leu Val
    1160                1165                1170

Leu Thr Ser Ile Asp Arg Arg Ile Ile Pro Val Glu Phe Phe Gly
    1175                1180                1185

Ser Arg Thr Val Leu Ile Leu Phe Ser Ser Thr Ala Ala Ala Gly
    1190                1195                1200

Ala Ala Ala Phe Val Pro Ile Tyr Met Leu Pro Leu Phe Phe Gln
    1205                1210                1215

Phe Thr Arg Gly Asp Gly Pro Leu Asp Ala Gly Val Arg Leu Leu
    1220                1225                1230

Pro Phe Ile Ile Leu Met Val Val Thr Ile Leu Thr Asn Gly Ala
    1235                1240                1245

Leu Leu Ser Lys Leu Gly Tyr Tyr Met Pro Trp Tyr Leu Met Gly
    1250                1255                1260

Gly Leu Leu Val Val Ala Gly Gly Ala Leu Met Tyr Thr Val Asp
    1265                1270                1275

Leu Ala Thr Ser Thr Ser Arg Ile Tyr Gly Tyr Thr Val Leu Met
    1280                1285                1290

Gly Val Gly Val Gly Ala Phe Ile Gln Ala Ser Phe Ala Val Ala
    1295                1300                1305

Gln Ala Val Val Glu Pro Glu Gly Val Pro Ala Ala Val Gly Phe
    1310                1315                1320

Ile Thr Leu Ala Gln Phe Ala Gly Ile Thr Ile Val Met Ala Ile
    1325                1330                1335

Ala Asn Ala Ile Phe Leu Asn Glu Cys Leu Ser Glu Ile Pro Lys
    1340                1345                1350

Ile Leu Pro Asn Val Ser Arg Ser Asp Ile Glu Ala Ala Ile Gln
    1355                1360                1365

Gly Thr Ser Asp Leu Leu Asp Thr Leu Ser Ser Glu Thr His Thr
    1370                1375                1380
```

```
Gln Val Leu Asn Ala Ile Val Ser Gly Ile Ser Lys Ala Tyr Ala
    1385            1390            1395

Leu Glu Ile Ala Ala Gly Ala Leu Val Ala Val Leu Ser Leu Leu
    1400            1405            1410

Met Lys Arg Glu Arg Leu Phe Gly Val Ser Ala Ala Val Ala Ala
    1415            1420            1425

Ala
```